(12) United States Patent
Krauland et al.

(10) Patent No.: US 9,550,809 B2
(45) Date of Patent: *Jan. 24, 2017

(54) HIGH AFFINITY METAL-OXIDE BINDING PEPTIDES WITH REVERSIBLE BINDING

(71) Applicant: Massachusetts Institute of Technology, Cambridge, MA (US)

(72) Inventors: Erik Mark Krauland, Lebanon, NH (US); Stephen Kottmann, Cambridge, MA (US); Roberto Juan Barbero, Cambridge, MA (US); Angela Belcher, Lexington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/034,420

(22) Filed: Sep. 23, 2013

(65) Prior Publication Data

US 2015/0259381 A1 Sep. 17, 2015

Related U.S. Application Data

(63) Continuation of application No. 12/678,911, filed as application No. PCT/US2008/077093 on Sep. 19, 2008, now Pat. No. 8,569,226.

(60) Provisional application No. 60/973,487, filed on Sep. 19, 2007.

(51) Int. Cl.
*C07K 7/08* (2006.01)
*C07K 14/245* (2006.01)
*A61K 38/00* (2006.01)

(52) U.S. Cl.
CPC ............... *C07K 7/08* (2013.01); *C07K 14/245* (2013.01); *A61K 38/00* (2013.01); *C07K 2319/24* (2013.01)

(58) Field of Classification Search
CPC ...................................................... C07K 7/08
See application file for complete search history.

(56) References Cited

U.S. PATENT DOCUMENTS 8,569,226 B2 * 10/2013 Krauland et al. ............... 514/1.1

FOREIGN PATENT DOCUMENTS

WO 92/19248 12/1992

OTHER PUBLICATIONS

Andrade et al., "Protein adsorption and materials biocompatibility—a tutorial review and suggested hypotheses," 1986, *Advances in Polymer Science*, 79: 1-63.
Bernard et al., "Printing patterns of proteins," 1998, *Langmuir*, 14(9): 2225-2229.
Burg et al., "Vacuum-packaged suspended microchannel resonant mass sensor for biomolecular detection." 2006, *J. Microelectromechanical Systems*, 15(6): 1466-1476.
Burg et al., "Weighing of biomolecules, single cells and single nanoparticles in fluid," 2007, *Nature*, 446(7139): 1066-1069.
Detrait et al., "Orientation of cell adhesion and growth on patterned heterogenous polystyrene surface," 1998, *J. Neurosci. Met.* 84(1-2): 193-204.
Dewez et al., "Adhesion of mammalian cells to polymer surfaces: from physical chemistry of surfaces to selective adhesion on defined patterns," 1998, *Biomaterials*, 19(16): 1441-1445.
Doh et al., "Immunological synapse arrays: patterned protein surfaces that modulate immunological synapse structure formation in t-cells," 2006, *PNAS*, 103(15): 5700-5705.
Granqvist et al., "Transparent and conducting ito films: new developments and applications," 2002, *Thin Solid Films*, 411(1): 1-5.
Horakova et al., "Luminometric method for screening retroviral protease inhibitors," 2005, *Anal. Biochem.*, 345(1): 96-101.
James et al., "Patterned protein layers on solid substrates by thin stamp microcontact printing," 1998, *Langmuir*, 14(4): 741-744.
Kane et al., "Patterning proteins and cells using soft lithography," 1999, *Biomaterials*, 20(23-24): 2363-2376.
Khademhosseini, et al., "Co-culture of human emboyonic stem cells with murine embryonic fibroblasts on microwell-patterned substrates," 2006, *Biomaterials*, 27(36): 5968-5977.
Kim et al., "Live lymphocyte arrays for biosensing," 2006, *Adv. Func. Mater.*, 16(10): 1313-1323.
Krauland, "Towards relational design of peptides for selective interaction with inorganic materials," 2007, Dissertation, MIT.
Langowski et al., "Microscale plasma-initiated patterning (mu pip)," 2005, *Langmuir*, 21(23): 10509-10514.
Lee et al., "Ordering of quantum dots using genetically engineered viruses," 2002, *Science*, 296(5569): 892-895.
Lhoest et al., "A new plasma-based method to promote cell adhesion on micrometric tracks on polystyrene substrates," 1996, *J. Biomater. Sci.—Polymer Ed.*, 7(12): 1039-1054.
Mao et al., "Viral assembly of oriented quantum dot nanowires," 2003, *PNAS*, 100(12): 6946-6951.
Mitchell et al., "Glow discharge modified tissue culture polystyrene: role of surface chemistry in cellular attachment and proliferation," 2006, *Surface Engineering*, 22(5): 337-344.
Mrksich et al. "Patterning self-assembled monolayers using microcontact printing: a new technology for biosensors?" 1995, *Trends in Biotech.*, 13(6): 228-235.
Raiteri et al., "Micromechanical cantilever-based biosensors," 2001, *Sensors and Actuators B-Chemical*, 79(2-3): 115-126.

(Continued)

*Primary Examiner* — Amber D Steele
(74) *Attorney, Agent, or Firm* — Steptoe & Johnson LLP

(57) ABSTRACT

A dodecamer peptide, and its modified variant, having a repeating glycine-lysine sequence was created and found to bind with high affinity to oxide surfaces and certain activated polymeric surfaces. Reversible binding characteristics of the peptides were demonstrated. The peptides were integrated with proteins, cells and fusion proteins to provide attachment of the proteins, cells and fusion proteins to solid material structures. The peptides can be used to functionalize surfaces of components within mechanical, biomechanical, micro fluidic, electronic, bioelectronic, bio-optical, and biochemical devices. Experiments were carried out to assess functionalization and reusability of a suspended mass resonator's cantilever.

20 Claims, 9 Drawing Sheets

(56) References Cited

OTHER PUBLICATIONS

Schmalenberg et al., "Microcontact printing of proteins on oxygen plasma-activated poly(methyl methacrylate)," 2004, *Biomaterials*, 25(10): 1851-1857.
Schmalenberg et al., "Micropatterned polymer substrates control alignment of proliferating Schwann cells to direction neuronal regeneration," 2005, *Biomaterials*, 26(12): 1423-1430.
Tamerler et al., "Adsorption kinetics of an engineered gold binding peptide by surface Plasmon resonance spectroscopy and a quartz crystal microbalance," 2006, *Langmuir*, 22(18): 7712-7718.
Tang et al., "Dynamic, electronically switchable surfaces for membrane protein microarrays," 2006, *Anal. Chem.*, 78(3): 711-717.
Van Kooten et al., "Plasma-treated polystyrene surfaces: model surfaces for studying cell-biomaterial interactions," 2004, *Biomaterials*, 25(10): 1735-1747.
Wang et al., "Microcontact printing of laminin on oxygen plasma-activated substrates for the alignment and growth of Schwann cells," 2007, *J. Biomed. Mater. Res B—Appl. Biomater.*, 80B(2): 447-453.
Weiner et al., "Design strategies in mineralized biological materials." 1997, *J. Mater. Chem.* 7: 689-702.
http://www.ncbi.nlm.nih.gov/protein/XP_362767 (Dean et al.).

\* cited by examiner

HIGH AFFINITY METAL-OXIDE BINDING PEPTIDES WITH REVERSIBLE BINDING

CROSS-REFERENCE TO RELATED U.S. APPLICATIONS

This application claims priority to U.S. Patent Application No. 60/973,487 filed on Sep. 19, 2007, which is incorporated by reference.

CLAIM OF PRIORITY

This application is a continuation of U.S. application Ser. No. 12/678,911, filed Mar. 18, 2010, which claims priority under 35 USC 371 to International Application No. PCT/US2008/077093, filed on Sep. 19, 2008, which claims priority to U.S. Provisional Application Ser. No. 60/973,487, filed Sep. 19, 2007, each of which is incorporated by reference in its entirety.

GOVERNMENT FUNDING

This invention was made with government support under Contract No. DAAD-19-03-D-0004 awarded by the Army Research Office. The government has certain rights in this invention.

FIELD OF THE INVENTION

The inventive embodiments relate to engineered peptides which reversibly bind with oxide surfaces. The inventive embodiments further relate to development of advanced compositions, materials and devices which utilize engineered peptides bound to non-natural oxide surfaces.

BACKGROUND

The study of biomolecules for biotechnology applications has gained widespread interest in recent years and potentially offers utilization of self-assembly and molecular recognition to develop and integrate advanced biotechnological materials into the medical and high-technology industries. The ability of biomolecules to direct the growth and organization of inorganic solids has been noticed in naturally-occurring biomineralization systems. (E. Baeuerlein, *Biomineralization: From Biology to Biotechnology and Medical Application*, Wiley-VCH, Weinheim, N.Y., 2000. S. Mann, *Biomineralization: Principles and Concepts in Bioinorganic Materials Chemistry*, Oxford chemistry masters, 5, Oxford University Press, Oxford, N.Y., 2001.) Natural biological systems have evolved diverse structures, e.g., bones, teeth, mollusk shells and magnetosomes, which exhibit greatly increased structural integrity compared to the organic scaffold from which they are formed. Natural systems can show exquisite control on the molecular scale, and biomineralized materials can surpass their chemically synthesized counterparts in certain physical characteristics such as hardness, fracture resistance, and abrasion resistance. Certain advantages of biomineralizing systems can include spatial and temporal control over growth, remodeling mechanisms, and synthesis of mineral phases not otherwise possible at low temperature and pressure. (S. Weiner and L. Addadi, "Design strategies in ineralized biological materials," *J. of Materials Chem.*, Vol. 7 (1997) pp. 689-702.)

One step toward emulating natural biomineralizing systems is to develop and identify certain biomolecules which can interact with, e.g., bind with, reversibly bind with, non-natural inorganic materials. In a controlled, laboratory environment, such biomolecules can be useful for the development of advanced biotechnological materials and systems.

SUMMARY

Two peptides are created and disclosed which bind in a reversible manner with oxide surfaces. A first peptide, denoted K1 (SEQ ID NO: 1), comprises the sequence GKGKGKGKGKGK (SEQ ID NO: 1). A second peptide, denoted 2K1 (SEQ ID NO: 2), comprises the sequence GKGKGKGKGKGKASGKGKGKGKGKGK (SEQ ID NO: 2). In various embodiments, either of the peptides can be bound to or attached to an oxide or plasma-activated surface. In various embodiments, a method for binding either inventive peptide to a surface comprises treating an oxide or plasma-activated surface with plural peptides wherein the peptides bind with or attach to the oxide or plasma-activated surface. The step of treating the oxide or plasma-activated surface can comprise exposing the oxide or plasma-activated surface to a solution containing a concentration of plural peptides. In certain embodiments, peptides K1 (SEQ ID NO: 1) or 2K1 (SEQ ID NO: 2) can be released from an oxide or plasma-activated surface. In various embodiments, a method for releasing bound peptides from a surface comprises exposing the bound peptides to a salt buffer so that the peptides release from the surface. The salt buffer can have a selected level of ionic strength. In certain embodiments, peptides K1 (SEQ ID NO: 1) or 2K1 (SEQ ID NO: 2) can be released from a surface by subjecting the bound peptides to an electric field or electrical bias. In various aspects, either inventive peptide K1 (SEQ ID NO: 1) or 2K1 (SEQ ID NO: 2) can be integrated with biomolecules, antimicrobial peptides, proteins, fusion proteins, biomineralizing proteins, anti-analytes or cells.

Peptides K1 (SEQ ID NO: 1) and 2K1 (SEQ ID NO: 2) can further be used to functionalize oxide or plasma-activated surfaces, and in particular inorganic oxide surfaces. As an example, the peptides can be integrated with proteins or cells and bound to oxide or plasma-activated surfaces on natural and non-natural materials. The bound constructs can be exposed to biomolecules which bind to the proteins or cells. In various embodiments, the peptides mediate the binding of various biomolecules, e.g., antimicrobial peptides, proteins, fusion proteins, anti-analyte molecules etc., to oxide or plasma-activated surfaces. The functionalized and/or bioactive surfaces can be incorporated in medical, electrical, magnetic, optical, biotechnology or high-technology devices.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

Figure 1A:
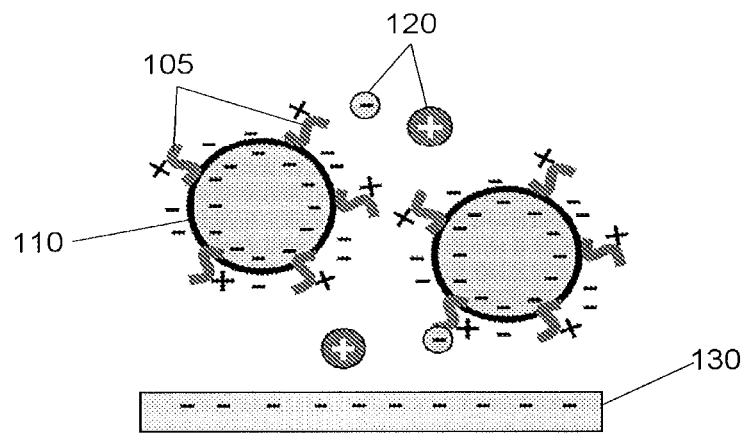
FIGS. 1A-1C depict biphasic binding behavior of the inventive peptides. The peptides 105 can be integrated with a host cell or protein 110.

The features and advantages of the present invention will become more apparent from the detailed description set forth below when taken in conjunction with the drawings.

DETAILED DESCRIPTION

In overview, two engineered peptides were developed and identified to bind with oxide or plasma-activated surfaces. In certain embodiments, the inventive peptides serve as binding agents for proteins cells to oxide or plasma-activated surfaces which are non-native to certain biological organisms and systems. Development of the peptides is described briefly. Measurements of their binding affinity, and methods for reversible binding of the peptides are presented. Integration of the peptides into advanced biotechnological systems is described.

I. Engineering of Peptides

An extensive study was carried out which led to the engineering of two peptides which bind in a reversible manner to a variety of oxide and plasma-activated surfaces. Details of the study are reported in the dissertation by Eric M. Krauland entitled, "Towards Ration Design of Peptides for Selective Interaction with Inorganic Materials," Massachusetts Institute of Technology, Cambridge, Mass., September, 2007, which is incorporated herein by reference. In brief, the investigations used a novel combination of yeast surface display (YSD), biopanning techniques, rational design methodology, and genetic engineering to arrive at two peptides having the desired properties of (1) binding to oxide or plasma-activated surfaces and (2) binding in a reversible manner. In certain embodiments, using rational design principles in conjunction with the other techniques, peptides can be engineered that adhere cells or proteins to oxide surfaces at strengths equivalent to those obtained for biopanning-enriched peptides while exhibiting much lower compositional complexity than the biopanning-enriched peptides.

One engineered peptide resulting from the study, denoted K1 (SEQ ID NO: 1), is a twelve amino acid long peptide containing a repeating lysine-glycine motif Its sequence is represented as GKGKGKGKGKGK (SEQ ID NO: 1). The peptide carries a net charge of +6. This peptide can exhibit a binding affinity to a sapphire surface with a dissociation constant of about 100 nanomolar (nM). The K1 (SEQ ID NO: 1) peptide can be engineered from annealed oligonucleotides, e.g., $G_6$ peptide oligos, with BstX1 compatible sticky ends ligated into BstX1 sites of pBPZ.

In overview, the dodecamer peptide can be prepared by genetically engineering oligos into a yeast display vector. Briefly, complementary oligos encoding the desired sequence and BstX1 overhangs are annealed and then ligated into a BstX1 digested pBPZ vector. Following electroporation into *E. coli* cells, Electromax DH10B (available from Invitrogen, Carlsbad, Calif.), colonies are grown and DNA extracted for sequence confirmation. Correctly constructed vectors are than transformed into EBY100 yeast using the Gietz quick transformation protocol and maintained on glucose-based media (SD media).

A second peptide resulting from the study, denoted 2K1 (SEQ ID NO: 2), contains two K1 (SEQ ID NO: 1) peptides that are connected by an alanine-serine linker sequence. Its sequence is represented as GKGKGKGKGKGKASGKGKGKGKGKGK (SEQ ID NO: 2). The peptide carries a net charge of +12. This peptide can exhibit a binding affinity to a sapphire surface with a dissociation constant of about 1 nM. The 2K1 (SEQ ID NO: 2) peptide can be engineered in a manner similar to that used for the K1 (SEQ ID NO: 1) peptide, although two K1 (SEQ ID NO: 1) sequences are linked together with the alanine-serine spacer. In various embodiments, the amino acids used to link the K1 (SEQ ID NO: 1) peptides are selected because the DNA that encodes for them includes an Nhe1 restriction enzyme site that can enable the original cloning strategy. Also in certain embodiments, the amino acids are selected because they encode for one neutral amino acid (Ala) and one hydrophilic amino acid (Ser).

II. Binding of Peptides to Oxide Surfaces

In various embodiments, the structures of peptides K1 (SEQ ID NO: 1) and 2K1 (SEQ ID NO: 2) facilitate their binding to oxide surfaces. The inventors postulate that improved binding in certain peptides can arise from peptide geometries that allow maximal alignment of basic amino acids towards a surface so that the charged groups within the peptide can undergo local electrostatic interactions with the surface oxide. In various aspects, peptides K1 (SEQ ID NO: 1) and 2K1 (SEQ ID NO: 2) bind to a variety of oxide surfaces, e.g., sapphire, quartz, thermally grown oxide on silicon, amorphous borosilicate glass, and other oxides, at high affinity and in a manner which can be selectively inhibited by high salt conditions and/or exposure to an electric field. In certain embodiments, the inventive peptides also bind in a reversible manner with plasma-activated surfaces, e.g., various polymeric surfaces subjected to an oxygen plasma. In various embodiments, the peptide 2K1 (SEQ ID NO: 2) and/or K1 (SEQ ID NO: 1) can be integrated with a selected protein, peptide, sequence or cell and function as a binding agent to bind the selected protein, peptide, sequence or cell to a targeted substrate surface. As used herein, the term "integrated with" includes, without being limited to, fusion or binding of the peptide with a protein, peptide, sequence or cell, as well as genetic expression of the peptide within the protein, peptide, sequence or cell. It will be appreciated that targeting proteins to oxide, metal oxide, or plasma-activated surfaces with peptide tags such as 2K1 (SEQ ID NO: 2) or K1 (SEQ ID NO: 1) may provide a facile one-step alternative coupling chemistry for the formation of protein bioassays and biosensors.

A method for binding the peptides to an oxide or plasma-activated surface can comprise treating an oxide or plasma-activated surface with plural peptides, e.g., K1 (SEQ ID NO: 1) and/or 2K1 (SEQ ID NO: 2), or peptide-tagged proteins or cells wherein the peptides bind or attach to the surface. The step of treating the surface can comprise exposing the surface to a solution containing the peptides or peptide-tagged proteins or cells. The solution may be a saline solution having a selected level of ionic strength. In certain embodiments, the ionic strength of the solution can be between about 1 nanomolar (nM) and about 10 nM, between about 10 nM and about 100 nM, between about 100 nM and about 1 micromolar (µM), between about 1 µM and about 10 µM, between about 10 µM and about 100 between about 100 µM and about 1 millimolar (mM), and yet in some embodiments, between about 1 mM and about 350 mM. The step of treating the oxide or plasma-activated surface can further comprise providing exposure of the surface to the solution for a selected period of time, and under selected conditions, e.g., temperature and agitation of solution. The method for binding the peptides or peptide-tagged proteins or cells to a surface can further comprise removing the surface from the solution containing the peptides after the selected period of time. In certain embodiments, the duration of the selected period of time and selected conditions can be chosen based upon a desired surface concentration of peptides or peptide-tagged proteins or cells bound to the surface.

In various embodiments, the peptides K1 (SEQ ID NO: 1) and/or 2K1 (SEQ ID NO: 2) can be integrated with a selected protein, peptide, sequence, or cell and function as a binding agent to bind the selected protein, peptide, sequence, or cell to a targeted substrate. In certain aspects, one or more peptide sequences K1 (SEQ ID NO: 1) and/or 2K1 (SEQ ID NO: 2) can be transferred from yeast to a model protein. As an example, the K1 (SEQ ID NO: 1) or 2K1 (SEQ ID NO: 2) peptides can be integrated with the maltose binding protein (MBP) by attachment to the end linker at the protein's c-terminus. Further details of a MBP-K1 construct are presented in Example 1. As another example, the K1 (SEQ ID NO: 1) or 2K1 (SEQ ID NO: 2) peptides can be integrated with yeast cells by genetically engineering oligos into a yeast vector. It will be appreciated that peptides which bind with high affinity to oxide or plasma-activated surfaces and can be integrated with a selected protein or cell can serve as an affinity tag for facile protein, biomolecule, or cell immobilization. In certain embodiments, affinity-tagged proteins, biomolecules, peptides, or cells are utilized in modified enzyme-linked immunosorbant assay (ELISA) systems. In Example 2 below, a modified ELISA is carried out with an affinity-tagged MBP to assess binding affinity of the tagged protein to certain oxide surfaces.

In certain embodiments, affinity-tagged proteins can serve as a basis to make affinity-tagged fusion proteins. For example, the affinity-tagged protein (MBP)-(2K1) can serve as a building block to create a variety of affinity-tagged fusion proteins. As an example, the affinity-tagged fusion protein (proteinA)-(MBP)-(2K1) can be made from (MBP)-(2K1) and can be used to immobilize certain antibodies to oxide surfaces. In such an example, the protein A component can function as an anti-analyte and the antibodies as analytes in a biochemical assay. In some embodiments, the affinity-tagged fusion proteins can be provided in an array, e.g., patterned on an oxide substrate or disposed in multiple wells of a multi-well plate, useful for ELISA or immunoassays. As another example, the affinity-tagged fusion protein (bFGF)-(MBP)-(2K1) can be made from (MBP)-(2K1) and can be used in a biosensor to monitor heparin content in blood samples.

In some embodiments, affinity-tagged fusion proteins are created which integrate antimicrobial peptides (AmP's). As an example, an antimicrobial peptide can be linked to an affinity-tagged protein, e.g., (AmP)-(MBP)-(2K1). In certain embodiments, the AmP is selected from the group consisting of: magainins, alamethicin, pexiganan, Template:MS1-78, Template:MS1-843, Template: MS1-594, Template: Polyphemusin, human antimicrobial peptide, and Template: LL-37, defensins, and protegrins. In some embodiments, other proteins, peptides, or sequences may be substituted for the linking protein MBP. As an example, a peptide with a sequence GGGGSGGGGSGGGGS (SEQ ID NO: 9) can be used in some embodiments to link an inventive peptide K1 (SEQ ID NO: 1) or 2K1 (SEQ ID NO: 2) to an AmP. In certain embodiments, a linking peptide will be flexible and have hydrophilic characteristics. The affinity-tagged antimicrobial fusion compositions can be attached to metal oxides or activated polymers and form antimicrobial peptide coatings. In various embodiments, a metal oxide or activated polymer surface can be functionalized with an affinity-tagged fusion composition and used to prevent bacterial adhesion and/or growth. In certain embodiments, the affinity-tagged antimicrobial fusion compositions are adapted to provide antimicrobial coatings for medical devices.

In various embodiments, peptides K1 (SEQ ID NO: 1) and 2K1 (SEQ ID NO: 2) can provide binding in a reversible manner to oxide surfaces. In certain embodiments, the binding of the peptides to an oxide surface can exhibit biphasic behavior. As an example and referring to FIG. 1, a peptide 105 may be integrated with a host protein 110 wherein the host protein carries a net negative charge. When the peptide and host protein are exposed to an oxide surface of a substrate 130 in a solution with low ionic strength, charge repulsion between the host protein and oxide surface can inhibit binding of the peptide to the surface. When the solution has an intermediate ionic strength, long range charge screening may occur and permit binding of the peptide to the oxide surface. At high levels of ionic strength, short range charge screening can occur and inhibit binding of the peptide to the oxide surface. Biphasic binding behavior can be advantageous in that is can allow for easy refurbishing of substrates and sensors by incubation of bound peptides in high-concentration salt buffers. Details and aspects of reversible binding by varying ionic strength are provided in Example 4.

Figure 1B:
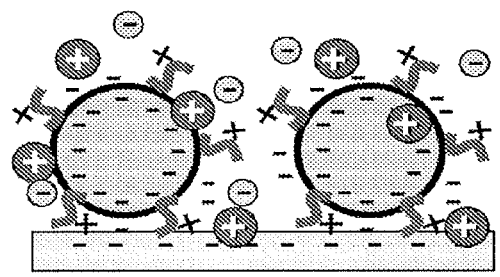
Figure 1C:
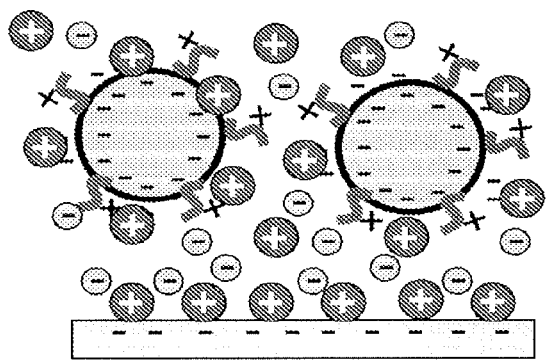

Referring again to FIGS. 1A-1C in further detail, peptides 105 can be integrated with a host protein or cell 110. In various embodiments, the peptides 105 carry a net positive charge. In certain embodiments, the host protein or cell 110 carries a net negative charge. In some embodiments, the host protein or cell 110 can carry a net positive charge or be charge neutral. When ionic strength of a solution, within which the peptide-tagged protein or cell is suspended, is low as shown in FIG. 1A, their can be insufficient free ions 120 to screen the host net charge from similar charge type on the surface of a substrate 130. In such a case, electrostatic repulsion can inhibit binding of the peptide-tagged protein or cell to the substrate 130. When the ionic strength of the solution is intermediate as depicted in FIG. 1B, free ions 120 can provide long-range charge screening and screen the net charge of the host protein or cell and permit binding of the peptides 105 to the substrate surface. At high ionic strengths, FIG. 1C, short-range charge screening can effectively screen all charges and inhibit peptide binding to the substrate surface.

A method for reversibly binding the peptides to an oxide surface can comprise treating an oxide or plasma-activated surface with plural peptides, e.g., K1 (SEQ ID NO: 1) and/or 2K1 (SEQ ID NO: 2), or peptide-tagged proteins or cells, wherein the peptides bind to the oxide or plasma-activated surface, and further subjecting the bound peptides to a salt buffer having a selected ionic strength so that the peptides release from the surface. The step of treating the surface can comprise exposing the surface to a solution containing the peptides or peptide-tagged proteins or cells. The solution may be a saline solution having a first level of ionic strength or salinity. The step of treating the surface can further comprise providing exposure of the surface to the solution containing the peptides for a selected period of time, and under selected conditions, e.g., temperature and agitation of solution. In various embodiments, the duration of the selected period of time and selected conditions can be chosen based upon a desired surface concentration of peptides or peptide-tagged proteins or cells bound to the surface. The step of subjecting the bound peptides or peptide-tagged proteins or cells to a salt buffer can comprise exposing the surface to a solution having a second level of ionic strength. The exposure of the bound peptides or peptide-tagged proteins or cells to the solution having a second level of ionic strength can be carried out for a selected period of time, and under selected conditions, e.g., temperature and agitation of solution. In various aspects, the second level of ionic strength is greater than the first level of ionic strength.

A first assessment of the binding affinity of the inventive peptides to oxide surfaces was carried out by the inventors using a yeast surface display (YSD) technique. In this study, peptides were expressed on the surface of yeast cells, and adhesion to sapphire substrates was measured. Additionally, the effect of charged residue placement along peptide sequences was evaluated. To this end, dodecamer peptides were designed and cloned onto the c-terminus of the Aga2 yeast display construct. Each designer peptide, listed in Table 1, contained six positively charged amino acids but varied either in type of residue (lysine (K) or arginine (R)) or the grouping of these residues along the peptide. Binding tests of the peptides against the A and R crystal faces of sapphire revealed two clear trends: First, lysine peptides bound better than identically constructed arginine peptides (e.g. K1>R1), and second, grouping charged residues decreased peptide binding (e.g. K1>K2>K3). These trends are evident from the measurements reported in FIG. 2A, which graphs percent area coverage (P.A.C.) of the bound yeast cells against the type of peptide. No clear preference for the A or R-face of sapphire was seen.

Figure 2A:
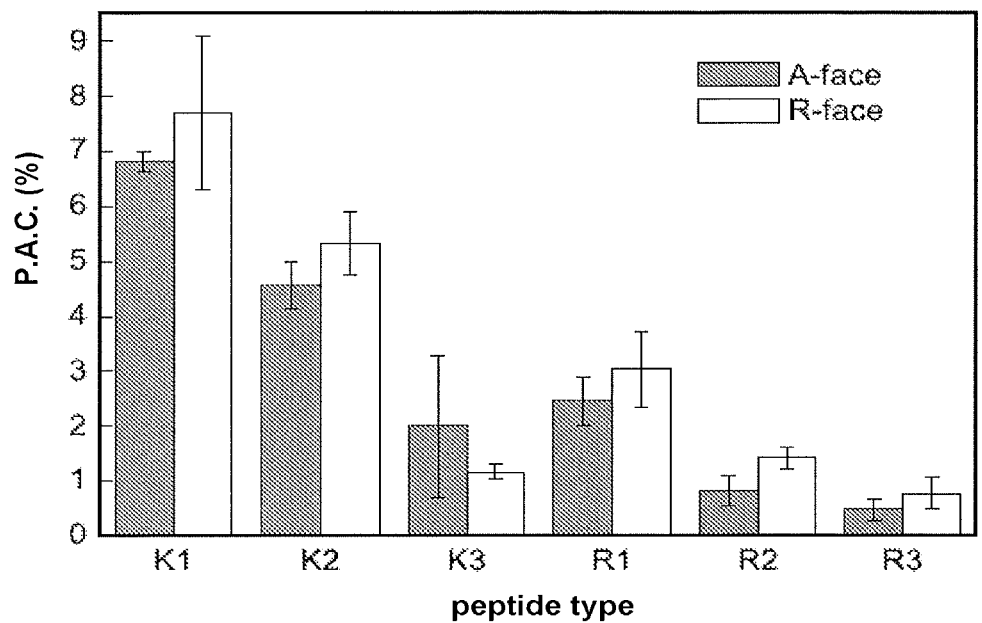
FIG. 2A shows experimental results of yeast clones with integrated peptide types of various residue grouping bound in PBS-BSAT to the A- (shaded) and R- (white) faces of sapphire. Each bar represents the average percent area coverage (P.A.C.) from two independent experiments and includes error bars representing the standard deviation. Percent area coverage (P.A.C.) is used as a measure of binding affinity.
Figure 2B:
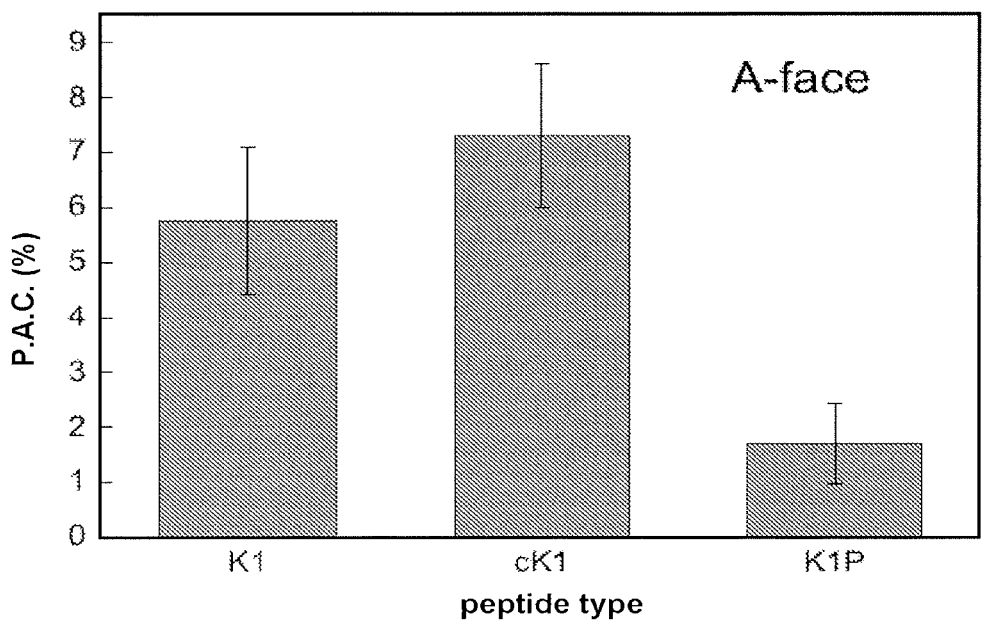
FIG. 2B shows results for variant forms of the K1 (SEQ ID NO: 1) peptide bound in PBS-BSAT to the A-face of sapphire. Each data point represents the average and standard deviation of binding from three independent experiments.

Two additional peptide variants of K1 (SEQ ID NO: 1) were designed and tested against the A-face of sapphire. The first, K1 (SEQ ID NO: 6), is the K1 (SEQ ID NO: 1) peptide flanked by cysteine residues that form a disulfide linkage in the oxidizing environment outside the cell and therefore constrain the alternating lysine residues into a loop. This peptide showed binding comparable, if not slightly better, than the unconstrained K1 (SEQ ID NO: 1) peptide as seen in the graph of FIG. 2B. The second peptide, K1P (SEQ ID NO: 7), in which the second, fourth, and sixth glycine residues of K1 (SEQ ID NO: 1) were replaced with proline, showed a significant decrease in cell binding over K1 (SEQ ID NO: 1).

TABLE 1

Peptide sequence information.

| name | sequence | SEQ ID NO: | net charge[a] | construct |
|---|---|---|---|---|
| stop | * | n/a | n/a | Aga2, MBP |
| X1 | GXGXGXGXGXGX* | 3 | +6 | Aga2, MBP |
| X2 | GGXXGGXXGGXX* | 4 | +6 | Aga2 |
| X3 | GGGXXXGGGXXX* | 5 | +6 | Aga2 |
| cK1 | CGKGKGKGKGKGKC* | 6 | +6 | Aga2 |
| K1P | GKPKGKPKGKPK* | 7 | +6 | Aga2 |
| 2K1 | (GK)$_6$AS(GK)$_6$ | 2 | +12 | MBP |

[a]at neutral pH
"*" denotes a stop codon
"X" denotes either lysine (K) or arginine (R)
Aga2: yeast surface display
MBP: N-terminal maltose binding protein Although such cell-based experiments cannot resolve the detailed molecular interaction, they can provide empirical evidence for the proposed interaction. From cell detachment assays, a clear trend is noticed between the basicity of the peptide and the interaction strength, which suggests the importance of multiple charge interactions. The importance of electrostatic interaction strength between peptide and surface can be shown empirically by two experiments. First, an altering of the ionic strength of a solution in which the peptides are suspended, which modulates electrostatic interactions by charge screening, can affect peptide-mediated cell or protein binding. Second, an altering of the type of residue along the peptide can provide experimental results suggestive of the relevance of charge distribution along the peptide. For example, the difference between lysine and arginine binding in designed peptides reported in FIG. 2A can result from differences in the localization of charge on the side-chain group. The positive charge in lysine is confined to a primary amine while in arginine it is delocalized in the guanidinium group. This delocalization may weaken salt bridges with anions on the sapphire surface as compared to lysine and therefore result in a weaker binding interaction. The guanidinium group can also become oxidized, which would eliminate the positive charge, and disrupt electrostatic interaction with the surface. In addition, access of the positively charged groups to the surface may be greater in lysine than arginine due to a longer alkyl chain connecting the peptide backbone to the charged moiety, as well as having a smaller charged moiety (amine versus guanidinium) in order to access surface specific grooves.

Without being bound by theory, the importance of side chain access to the surface may be deduced empirically from binding experiments with the designed peptides. In a linear peptide chain, alternating amino acid side chain groups can orient in opposite directions. Therefore, in neighboring amino acids it is energetically unfavorable to align side chains. Grouping of charged residues into neighboring amino acids, going from sequence K1 (SEQ ID NO: 1) to K2 (SEQ ID NO: 4) to K3 (SEQ ID NO: 5), would decrease the ability of peptides to align charged residues and may result in the observed decrease in binding. As the basic amino acids are grouped, it also leads to a decrease in charge coverage over the surface. This decrease in surface coverage is not believed to be a factor because constrained peptide K1 (SEQ ID NO: 6) bound to the oxide with an affinity on the order of that found for K1 (SEQ ID NO: 1) while being constrained to a smaller net surface area. (See FIG. 2B.) Additional evidence for the importance of charge alignment can be found from the introduction of rigid kinks in the peptide backbone with proline residues, e.g., clone K1P (SEQ ID NO: 7), and the resulting decrease in peptide-mediated cell binding. From an engineering perspective, the results of FIGS. 2A-2B are encouraging because they suggests the ability to tune the affinity of a peptide by simply changing the number of charged groups or the flexibility of the backbone. In addition, the binding could be modulated by altering the ionic strength of the buffer, an aspect explored in Example 4 below.

Although the inventive peptides show affinity for oxide surfaces, it will be clear from the experiments and examples that the peptides can also attach to activated surfaces. In certain embodiments, the peptides bind with plasma-activated surfaces. In some embodiments, plasma-activated surfaces can be obtained by exposing a surface of a material to an oxygen plasma. In certain embodiments, polymeric surfaces can be activated by exposure to an oxygen plasma. As an example, surfaces of polymers such as polystyrene, polydimethylsiloxane, polyurethane, polycarbonate, and poly(methyl methacrylate) can be activated in an oxygen plasma such that the inventive peptides attach to these surfaces. In some embodiments, a polymeric surface coating may be applied to a material, object or device, and the polymeric surface coating activated in an oxygen plasma so that the inventive peptides attach to the surface coating. A polymeric surface coating may be established by methods of spin coating, dip coating, spray coating, vacuum deposition or similar coating techniques.

III. Integration of Peptides into Advanced Systems

The ability to coat surfaces with functional proteins, biomolecules, or cells can be useful for the construction and development of biosensors, bioassays and advanced biotechnological systems. Since oxide surfaces, such as $SiO_2$, or plasma-treated polymers, are common substrates in biological applications, an oxide-binding peptide, such as 2K1 (SEQ ID NO: 2) or K1 (SEQ ID NO: 1), with an ability to adhere proteins with nanomolar affinity, may be a useful candidate as a versatile affinity tag. Methods of using the inventive peptides 2K1 (SEQ ID NO: 2) or K1 (SEQ ID NO: 1) to create protein-functionalized oxide surfaces are described. This section highlights several ways in which 2K1 (SEQ ID NO: 2) can be used to immobilize proteins to oxide-surfaces. In particular, two methods of micro-scale patterning of 2K1-tagged MBP are described. The methods utilize soft-lithography techniques. Additionally, a method to selectively inhibit tagged-protein from electronically-biased surface, e.g., indium tin oxide (ITO) electrodes, is described. Also, the utility of 2K1-tagged MBP in functionalizing a novel mass-based biosensor is demonstrated.

III-A. Micropatterning of Affinity-Tagged Proteins

The ability to functionalize surfaces on the micro-scale with biologically active molecules has shown utility in biotechnical areas including stem cell biology (A. Khademhosseini, L. Ferreira, J. Blumling, J. Ych, J. M. Karp, J. Fukuda, and R. Langer, "Co-culture of human embryonic stem cells with murine embryonic fibroblasts on microwell-patterned substrates," *Biomaterials*, Vol. 27, No. 36 (2006) pp. 5968-5977) and neurobiology (K. E. Schmalenberg and K. E. Uhrich, "Micropatterned polymer substrates control alignment of proliferating schwann cells to direct neuronal regeneration," *Biomaterials, Vol.* 26, No. 12 (2005) pp. 1423-1430) and immunology (J. Doh and D. J. Irvine, "Immunological synapse arrays: Patterned protein surfaces that modulate immunological synapse structure formation in t cells," *Proceedings of the National Academy of Sciences of the United States of America*, Vol. 103, No. 15 (2006) pp. 5700-5705; H. Kim, R. E. Cohen, P. T. Hammond, and D. J. Irvine, "Live lymphocyte arrays for biosensing," *Advanced Functional Materials*, Vol. 16, No. 10 (2006) pp. 1313-1323). Most biological microscale patterning techniques utilize a form of soft lithography termed micro-contact printing (μCP). Initially developed for patterning self-assembled monolayers by George Whitesides group (M. Mrksich and G. M. Whitesides, "Patterning self-assembled monolayers using microcontact printing—a new technology for biosensors," *Trends in Biotechnology*, Vol. 13, No. 6 (1995) pp. 228-235), it was first applied to direct protein patterning in 1998 (A. Bernard, E. Delamarche, H. Schmid, B. Michel, H. R. Bosshard, and H. Biebuyck, "Printing patterns of proteins," *Langmuir*, Vol. 14, No. 9 (1998) pp. 2225-2229; and C. D. James, R. C. Davis, L. Kam, H. G. Craighead, M. Isaacson, J. N. Turner, and W. Shain, "Patterned protein layers on solid substrates by thin stamp microcontact printing," *Langmuir*, Vol. 14, No. 4 (1998) pp. 741-744). In general, this approach involves (1) creating a polydimethylsiloxane (PDMS) elastomer "stamp" from a photolithographically patterned silicon wafer, (2) adsorbing a biomolecule on the PDMS stamp, then (3) transferring the biolomolecule to a desired substrate by contact printing. (R. S. Kane, S. Takayama, E. Ostuni, D. E. Ingber, and G. M. Whitesides, "Patterning proteins and cells using soft lithography," *Biomaterials, Vol.* 20, No. 23-24 (1999) pp. 2363-2376) This general procedure was used to guide the development two schemes, depicted in FIGS. 7A-7B, for micropatterning affinity-tagged proteins on oxide surfaces.

The first scheme, termed microscale plasma-initiated patterning (μPIP), involves first patterning the surface of a substrate using a mask and a plasma, and then incubating the substrate with a protein that selectively attaches to the plasma-treated surface. (B. A. Langowski and K. E. Uhrich, "Microscale plasma-initiated patterning (mu pip)," *Langmuir*, Vol. 21, No. 23 (2005) pp. 10509-10514) This method, depicted in FIG. 7A, was used to bind MBP-2K1 to $O_2$-plasma-treated regions of a polystyrene substrate. Briefly, a PDMS mold 710 was used to mask selected regions of a polystyrene (PS) surface of a substrate 720. Next, the substrate was treated with an $O_2$-plasma, which oxygenates exposed regions into a highly electronegative hydrophilic surface. The PDMS mold was then removed to expose both PS and plasma-treated polystyrene (PT-PS). Affinity-tagged protein MBP-2K1, which has nanomolar affinity toward oxygenated PS, was then incubated with the substrates, e.g., exposed in solution to the substrate. The substrate can then be subjected to a rinse or cleansing bath which removes unbound tagged proteins. A micrograph in FIG. 7A demonstrates adhesion of immuno-stained MBP-2K1 to a PT-PS region (light area) and substantially no adhesion of the tagged protein to an untreated PS region (dark area). Further details of μPIP with the inventive peptides are provided in Example 5.

In various embodiments, the μPIP method for micropatterning affinity-tagged proteins on oxide surfaces comprises placing a PDMS mold or mask in contact with a surface of a substrate. In some embodiments, the mask may be a topographically-patterned mask or a stencil mask. The μPIP method can further comprise exposing the substrate with contacted mask to a plasma, e.g., and oxygen plasma. The μPIP method can further comprise removing the PDMS mask, and incubating or exposing the substrate to a solution containing affinity-tagged proteins, biomolecules or cells. The substrate can be exposed to the solution for a selected period of time. The ionic strength of the solution can be a selected level. The μPIP method can further comprise rinsing the substrate with a cleansing rinse, so as to remove unbound affinity-tagged proteins, biomolecules or cells from the substrate.

The μPIP method can benefit from certain optimizations. First, a PDMS mold or mask does not allow for facile patterning on the microscale. If a topographically-patterned mask is used, the short-lived plasma-induced reactive species cannot penetrate at long ranges into microchannels formed under the mask when placed in contact with the substrate. Although stencil masks can mitigate this problem, a need for support structures in stencil masks can limit available pattern shapes, e.g., an annulus shape can only be obtained by adding radial supports in a stencil mask. Other lithographic techniques, which may aid patterning, have been described to patterned PT-PS features into PS. (J. B. Lhoest, E. Detrait, J. L. Dewcz, P. V. deAguilar, and P. Bertrand, "A new plasma-based method to promote cell adhesion on micrometric tracks on polystyrene substrates," *Journal of Biomaterials Science-Polymer Edition*, Vol. 7, No. 12 (1996) pp. 1039-1054; S. A. Mitchell, M. R. Davidson, and R. H. Bradley, "Glow discharge modified tissue culture polystyrene: role of surface chemistry in cellular attachment and proliferation," *Surface Engineering*, Vol. 22, No. 5 (2006) pp. 337-344.) Additionally, the μPIP prepatterning method is somewhat limited to materials that can be oxygenated or activated with plasmas or UV/ozone treatment. Such materials comprise mainly carbonaceous polymers. However, given the inherent cell adhesion properties of plasma-treated polymers, specifically PT-PS over PS, e.g., as disclosed in (E. Detrait, J. B. Lhoest, B. Knoops, P. Bertrand, and P. V. D. de Aguilar, "Orientation of cell adhesion and growth on patterned heterogeneous polystyrene surface," *Journal of Neuroscience Methods*, Vol. 84, No. 1-2 (1998) pp. 193-204; J. L. Dewez, J. B. Lhoest, E. Detrait, V. Berger, C. C. Dupont-Gillain, L. M. Vincent, Y. J. Schneider, P. Bertrand, and P. G. Rouxhet, "Adhesion of mammalian cells to polymer surfaces: from physical chemistry of surfaces to selective adhesion on defined patterns," *Biomaterials*, Vol. 19, No. 16 (1998) pp. 1441-1445; T. G. van Kooten, H. T. Spijker, and H. J. Busscher, "Plasma-treated polystyrene surfaces: model surfaces for studying cell-biomaterial interactions," *Biomaterials*, Vol. 25, No. 10 (2004) pp. 1735-1747), adding the ability to selectively target proteins to the PT-PS with the inventive affinity tags should greatly increase the functionality of these systems.

Figure 7A:
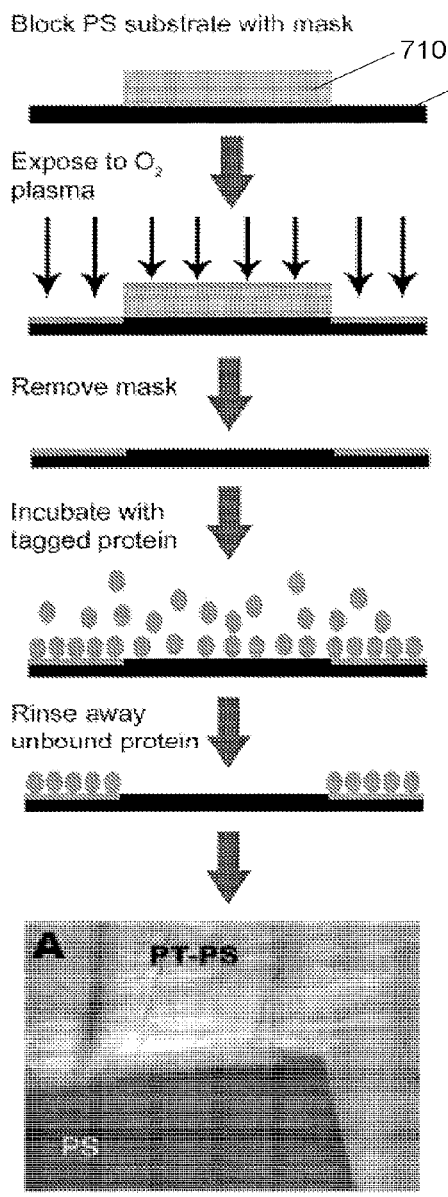
FIGS. 7A-7B depict methods for and results from surface micropatterning of affinity-tagged proteins. Two methods for patterning peptide-tagged proteins onto oxide surfaces are shown. (7A) For micro-plasma-initiated patterning (μPIP), a hydrophobic organic surface, such as polystyrene (PS), is masked with a PDMS mask in a desired pattern. The exposed surface area of the PS is activated with a plasma. The mask is then removed and the affinity-tagged proteins preferentially bind to the activated surface. Unbound proteins can be rinsed away. (7B) For microcontact printing (μCP), affinity-tagged proteins are first bound to an activated polydimethylsiloxane (PDMS) stamp that is topographically micropatterned using soft-lithography techniques. The mask is then placed in intimate contact with a substrate. The protein can then bind to and be transferred to an oxide surface. (7A micrograph) Immuno-labeled MBP-2K1 is shown, imaged using a 40× objective lens, selectively bound to plasma-treated polystyrene (PT-PS), light area. Substantially no affinity-tagged proteins bind to the previously covered area, dark area. (7B micrograph) Immuno-labeled MBP-2K1 transferred to tissue-culture-treated polystyrene using μCP. Affinity-tagged proteins are transferred in the light area, where the PDMS was in intimate contact with the substrate during the printing step. Substantially no proteins are transferred where the mask was not in contact with the substrate.
Figure 7B:
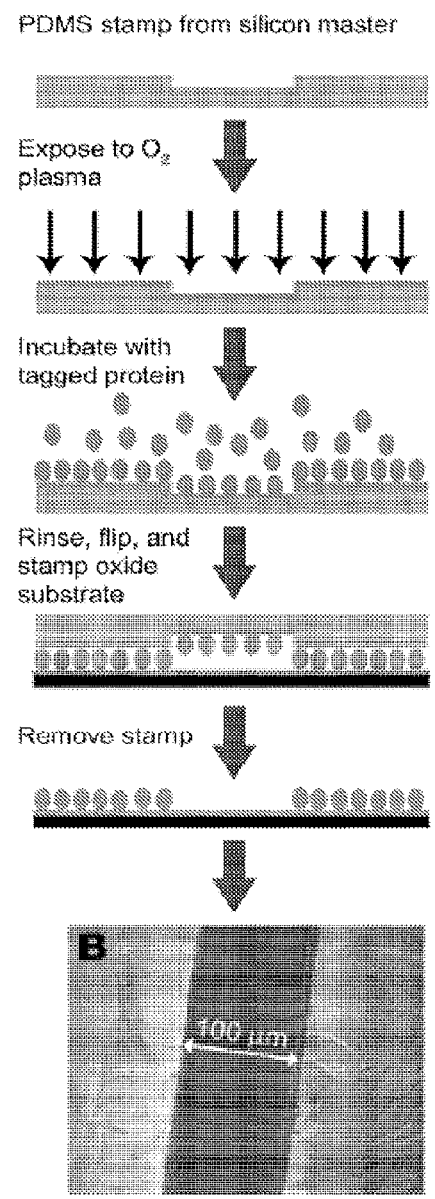

The second patterning method shown in FIG. 7B is similar to traditional microcontact printing (μCP) and has been used by the inventors to pattern MBP-2K1 onto tissue-culture-treated polystyrene (TCT-PS). Briefly, a PDMS stamp is activated by exposure to $O_2$-plasma and incubated with MBP-2K1. After incubation with protein and subsequent washes, the stamp is pressed onto TCT-PS. At regions of contact between the mask and substrate, the affinity-tagged protein can transfer from the mask to the substrate. A micrograph in FIG. 7B shows a TCT-PS treated surface immuno-stained for MBP. Two regions (light areas) of protein deposition are clearly observed flanking a protein deficient 100-μm-wide channel (dark area). Variations of the procedure showed that both the peptide 2K1 (SEQ ID NO: 2) integrated with MBP and the PDMS activation step are necessary for the efficient stamping of MBP-2K1 onto TCT-PS. (Data not show for trials without 2K1 (SEQ ID NO: 2) and without PDMS activation.) Microcontact printing has been used to micropattern laminin onto plasma-treated PMMA for the alignment and growth of Schwann cells. (K. E. Schmalenberg, H. M. Buettner, and K. E. Uhrich, "Microcontact printing of proteins on oxygen plasma-activated poly(methyl methacrylate)," *Biomaterials*, Vol. 25, No. 10 (2004) pp. 1851-1857; and D. Y. Wang, Y. C. Huang, H. S. Chiang, A. M. Wo, and Y. Y. Huang, "Microcontact printing of laminin on oxygen plasma activated substrates for the alignment and growth of schwann cells," *Journal of Biomedical Materials Research Part B—Applied Biomaterials*, Vol. 80B, No. 2 (2007) 447-453.) Additional details of μCP with the inventive peptides are provided in Example 6.

In various embodiments, a method for μCP patterning of oxide surfaces with the inventive peptide-tagged proteins, biomolecules or cells comprises providing a patterned PDMS stamp, and activating the surface of the stamp, e.g., by exposing it to plasma, so that the peptides bind with the activated surface of the stamp. The method for μCP patterning can further comprise incubating the PDMS stamp with affinity-tagged proteins, biomolecules or cells for a selected period of time, and subjecting the PDMS stamp to a rinse which removed unbound proteins or cells. The method for μCP patterning can further comprise placing the PDMS stamp in contact with a substrate to be patterned, and leaving the stamp in contact with the substrate for a selected period of time. The method for μCP patterning can further comprise removing the PDMS stamp from the substrate.

In general, printing methods involving plasma treatment can be easier to implement, more cost effective, less labor intensive, and more environmentally friendly than wet chemical methods. In addition, plasma activation of a PDMS stamp can decrease the protein equilibration time over the more common hydrophobic PDMS surfaces. (A. Bernard, E. Delamarche, H. Schmid, B. Michel, H. R. Bosshard, and H. Biebuyck, "Printing patterns of proteins," *Langmuir*, Vol. 14, No. 9 (1998) pp. 2225-2229.) Hydrophobic adsorption to the stamps may also lead to unwanted denaturing of the protein of interest. (J. D. Andrade and V. Hlady, "Protein adsorption and materials biocompatibility—a tutorial review and suggested hypotheses," *Advances in Polymer Science*, Vol. 79 (1986) pp. 1-63.) The additional functionality offered by the inventive peptide affinity tags, such as 2K1 (SEQ ID NO: 2) or K1 (SEQ ID NO: 1), for selectively adhering to plasma-treated surfaces should greatly expand the repertoire of proteins suitable for μCP, including extremely soluble proteins like MBP, without the requirement for long incubation times as required with hydrophobic surfaces.

III-B. Electronic Removal of Affinity-Tagged Proteins

Surfaces that respond to electrical stimulus can be useful for advanced systems utilizing the inventive peptides, since they offer the potential to electrically modulate peptide binding. Also they may enable facile integration of advanced biotechnological systems which include the inventive peptides with well-established microelectronic devices. In certain embodiments, microelectronic devices can provide superior temporal resolution for the biotechnological systems. Recently, it has been shown that poly-L-Lysine-grafted-polyethylene glycol (PLL-g-PEG) can be electrochemically desorbed from indium tin oxide (ITO) surfaces. (C. S. Tang, M. Dusseiller, S. Makohliso, M. Hcuschkel, S. Sharma, B. Keller, and J. Voros, "Dynamic, electronically switchable surfaces for membrane protein microarrays," *Analytical Chemistry*, Vol. 78, No. 3 (2006) pp. 711-717.) ITO surfaces are potential candidates for biosensors due to their low electrical resistivity and high optical transparency. (C. G. Granqvist and A. Hultaker, "Transparent and conducting ito films: new developments and applications," *Thin Solid Films*, Vol. 411, No. 1 (2002) pp. 1-5.) Although the mechanism of protein removal with applied positive bias is not currently understood, it has been hypothesized to be due to either, accumulated positive surface charge repelling positively adsorbed molecules, or oxygen generated from electrolysis that reacts with adsorbed molecules and changes the physiochemical properties leading to adsorption. (C. S. Tang, et al.)

Given the oxide binding properties and presence of multiple lysine residues in PLL and the affinity tag 2K1 (SEQ ID NO: 2), the inventors postulated that a protein or cell tagged with the inventive peptides, e.g., 2K1-MBP, might be adapted for electrochemical desorption from ITO. FIGS. 8A-8D depict an experimental setup and results from 2K1-MBP desorption experiments. Details of an experiment carried out with such apparatus are presented in Example 7.

In various embodiments, ITO films on a glass substrate are etched to pattern electrically isolated electrodes 810. Affinity-tagged proteins 820 are then incubated with the ITO electrodes, while simultaneously biasing one or more electrodes. The bias can be applied for a selected period of time and subsequently removed. The substrate can be extracted from the incubating solution and washed with a cleansing rinse which removes unbound affinity-tagged proteins, biomolecules or cells. Details and results from experiments carried out to demonstrate electrochemical modulation of surface attachment for the inventive peptides are provided in Example 7.

The ability to selectively adsorb affinity-tagged proteins onto electrode surfaces can be useful for the facile construction of protein arrays. An advantage of using affinity-tagged proteins over PLL-g-PEG-biotin/Ni-NTA, is that fewer processing steps are involved to deposit proteins. For applications requiring large arrays or large numbers of arrays, cutting the number of steps in one deposition cycle would significantly decrease the overall processing time. Another advantage is the possibility for lower applied potentials, due to the smaller size of affinity tags like 2K1 (SEQ ID NO: 2) or K1 (SEQ ID NO: 1) versus PLL. Advantages of a PLL-g-PEG system over affinity-tagged proteins can be inherent anti-fouling properties of PEG, as well as the potential to functionalize one PLL-g-PEG chain many times and therefore increase protein packing density. In some embodiments, a system comprising a combination of affinity-tagged proteins and PLL-g-PEG may provide faster and more versatile protein array construction.

III-C: Functionalization of Suspended Mass Resonators (SMR)

Figure 9A:
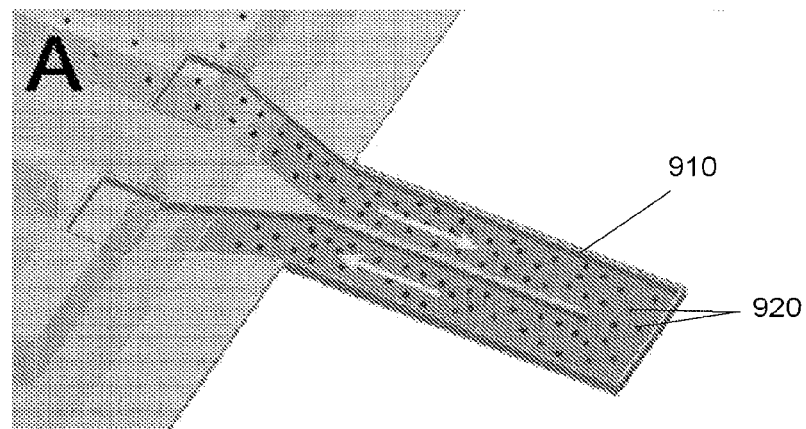
FIG. 9A is a pan-view illustration of a portion of a suspended mass resonator (SMR) mass sensor. The SMR's cantilever 910 is shown which contains microfluidic channels. Affinity-tagged proteins 920 can be introduced to and removed from the cantilever through the channels.

With advances in microfluidic and microfabrication techniques, there has been a recent trend towards miniaturization of biosensors. (R. Raiteri, M. Grattarola, H. J. Butt, and P. Skladal, "Micromechanical cantilever-based biosensors," *Sensors and Actuators B—Chemical*, Vol. 79, No. 2-3 (2001) pp. 115-126.) Advantages of these systems include high sensitivity, label-free sensing, small handling volumes, and parallelization. Recently, Burg et al. developed a microfabricated mass sensor using a fluid-filled cantilever with reported mass sensitivities down to approximately 300 attograms. (T. P. Burg, M. Godin, S. M. Knudsen, W. Shen, G. Carlson, J. S. Foster, K. Babcock, and S. R. Manalis, "Weighing of biomolecules, single cells and single nanoparticles in fluid," *Nature*, Vol. 446, No. 7139 (2007) pp. 1066-1069.) A schematic of such a microfabricated sensing mechanism is depicted in FIG. 9A. In various embodiments, the cantilever 910 of a suspended mass resonator (SMR) is driven to vibrate at its resonance frequency and the vibrating cantilevered arm is monitored optically with a laser. As molecules are flowed into the cantilever, changes in effective mass of the cantilever can be detected as a change in the arm's resonance frequency. An increase in mass due to accumulation of adsorbed molecules on the walls, or the presence of large dense particles, can alter the resonance frequency of the cantilever. The alteration of resonance frequency can be detected by the optical monitoring system and provide a signal representative of a change in mass. In this manner, an SMR can measure adsorbed antibodies as well as single gold and bacteria particles. (T. P. Burg, et al.)

Although a highly sensitive and versatile technique, a challenge for SMR, and other surface sensing techniques such as surface plasmon resonance (SPR) and quartz crystal microbalance (QCM), is the ability to perform facile and specific surface functionalization. Traditional techniques aimed at functionalization utilize covalent bonding methods, such as thiol linkages to gold or silanization of oxide surfaces. Although these techniques can form highly stable surfaces, these methods are typically irreversible and therefore limit the versatility and lifetime of the device, especially for many microfabricated sensors, such as the SMR, in which the sensing surface is directly integrated into the whole apparatus.

In one approach, PLL-g-PEG-biotin polymers were used to functionalize an SMR. The highly positively charged nature of PLL can bind to the native surface oxide of silicon in the cantilever of the SMR. This polymer has been used to adhere biotinylated antibodies through a neutravidin intermediary layer. (T. P. Burg, et al.) Unfortunately, this process involves multiple steps that can be both time consuming and hard to standardize.

Since the inventive peptides 2K1 (SEQ ID NO: 2) and K1 (SEQ ID NO: 1) can provide reversible binding with oxide or oxygen activated surfaces, the inventors postulated that they may be useful to biological functionalize an SMR and adapt it for reusable operation. Such an SMR can be versatile in that is could be readily adapted to a variety of mass sensing applications. In various embodiments, the functionalization is stable over the course of an experiment, non-fouling, versatile in conferring specificity, and facile in preparation. In various embodiments, functionalization with reusable operation is provided by a protein, biomolecule or cell layer that contains a genetically encoded surface-affinity peptide, wherein the protein, biomolecule or cell layer is reversibly bound to an oxide surface or activated surface within an SMR cantilever. An advantage to using the inventive peptides for SMR is that they can provide non-covalent binding schemes to oxide surfaces in an SMR. Additionally, the functionalization process can be monitored and modified in real time, e.g., modification can be achieved by changing ionic strength of the solution and/or application of electrical potentials. This can allow for faster optimization, better quality control, and more consistency between multiple functionalizations. Further, functionality can be added to the inventive peptide tag construct, e.g., protein fusion can be employed to add a specific receptor or biomolecule for analyte sensing. As an example, protein A can be added to the MBP-2K1 construct and reversibly bound to an SMR to provide facile antibody capture and detection.

Experiments demonstrating functionalization of an SMR device were carried out, and results are reported in Example 8.

IV. Applications

The inventive peptides can be used for a variety of biotechnological applications. It will be appreciated that certain advantages of the inventive peptides suggest applications relating to material-specific biomolecules. First, as described above, is an application as peptide affinity tags for facile surface functionalization with proteins, biomolecules or cells. The inventive peptides can be integrated with proteins, biomolecules or cells and mediate binding to specific surfaces. In some embodiments, the peptides can alleviate or eliminate a need for prior chemical surface functionalization, and their non-covalent attachment characteristic can be useful for multi-purpose surfaces offering reusability. Such surfaces can include microfabricated sensors, such as the SMR, micropatterned surfaces, oxide or polymeric surfaces, and bioseparation resins. In some embodiments, an inventive peptide can be integrated with or fused with a material-specific biomolecule, e.g., a biomineralizing protein. The fused peptide-biomineralizing protein can be used to selectively direct the nucleation and growth of certain inorganic constructs on prepatterned or unpatterned substrates. Used in only two ways, as affinity tags and nucleation tags, material-specific peptides have the potential to impact fields as diverse as medicine, biotechnology, and electronics.

Currently, only a few peptide affinity tags, such as the polyhistidine tag, directly recognize and bind with a solid support for protein purification systems. Identifying other tags that specifically recognize common materials such as silica and alumina can greatly increase the versatility of bioseparation systems while decreasing their cost. In certain embodiments, the inventive peptides 2K1 (SEQ ID NO: 2) and/or K1 (SEQ ID NO: 1) are used in separation and purification technologies. As an example, the inventive peptides can be used in chromatography or affinity-based purification systems. The inventive peptides can be used as an alternative or supplement to hexa-histidine/nickel-based separation and purification systems.

Peptide-tagged proteins can be fused with other proteins, biomolecules or cells for use in biochemical assays or biosensors. In various embodiments, the fusion proteins, biomolecules or cells can be used to immobilize other biomolecules, e.g., antibodies, analytes, antimicrobial peptides, etc. The inventors have created two fusion proteins to demonstrate such applications. The fusion proteins created were (protein A)-(MBP)-(2K1) and (bFGF)-(MBP)-(2K1). In certain embodiments, (protein A)-(MBP)-(2K1) can be used to immobilize antibodies or analytes. For example, the affinity-tagged MBP of the fusion protein can bind to an oxide surface. The bound fusion protein can be exposed to a solution containing a concentration of antibodies or analytes, e.g., hCG, which can bind with protein A. In certain embodiments, (bFGF)-(MBP)-(2K1) can be used in a similar manner to monitor heparin content in blood samples. Both fusion proteins can be used in assay or biosensor devices, and the devices may be reusable due to the reversible binding characteristics of the inventive peptides. For example, after an assay or biosensor has been exposed to a target antibody, analyte, biomolecule, or cell, the bioactive oxide surfaces of the apparatus can be flushed with a high salt solution to release bound peptides from oxide surfaces. In some embodiments, an electrical bias may be applied to the oxide surfaces to aid removal of bound peptides.

Another potential use of material-specific peptides is the supramolecular organization of inorganic material on biological scaffolds. The ability to site-specifically place peptides at unique places on biological scaffolds can add versatility to supramolecular organization. Aspects of such a technique have been demonstrated by the ability to organize quantum dots or create nanowires on the same organism by utilizing different peptide attachment schemes. (S. W. Lee, C. Mao, C. E. Flynn, and A. M. Belcher, "Ordering of quantum dots using genetically engineered viruses," *Science*, Vol. 296, No. 5569 (2002) pp. 892-895; C. Mao, C. E. Flynn, A. Hayhurst, R. Sweeney, J. Qi, G. Georgiou, B. Iverson, and A. M. Belcher, "Viral assembly of oriented quantum dot nanowires," *Proc Natl. Acad Sci USA*, Vol. 100, No. 12 (2003) pp. 6946-6951.) Peptide-based nucleation on biological scaffolds may also prove useful in low energy, large-scale production of inorganic materials.

The inventive peptides can be used to attach biomolecules to biologically directed architectures. Affinity-tagged fusion proteins can be used, following the methods described above, to functionalize metal oxide surfaces of implantable medical devices. The inventive peptides can be used, following the methods described above, to create antimicrobial surfaces by facilitating the attachment of one or more antimicrobial peptides to an oxide surface. The inventive peptides can be used to functionalize the surfaces of cell culture plates with biomolecules. In some embodiments, the inventive peptides are used to attach biomolecules to certain components within electronic, mechanical or chemical devices. For example, the peptides can be used to attach biomolecules to solar cells, certain components of fuel cells, battery electrodes or charge storage media, transistors, magnetic or electronic memory cells, or catalysts. In certain embodiments, the attached biomolecules and biologically directed architectures can improve operability and/or durability of the device in which they are incorporated.

EXAMPLES

Example 1

Peptide Mediated Adhesion of MBP

Figure 3A:
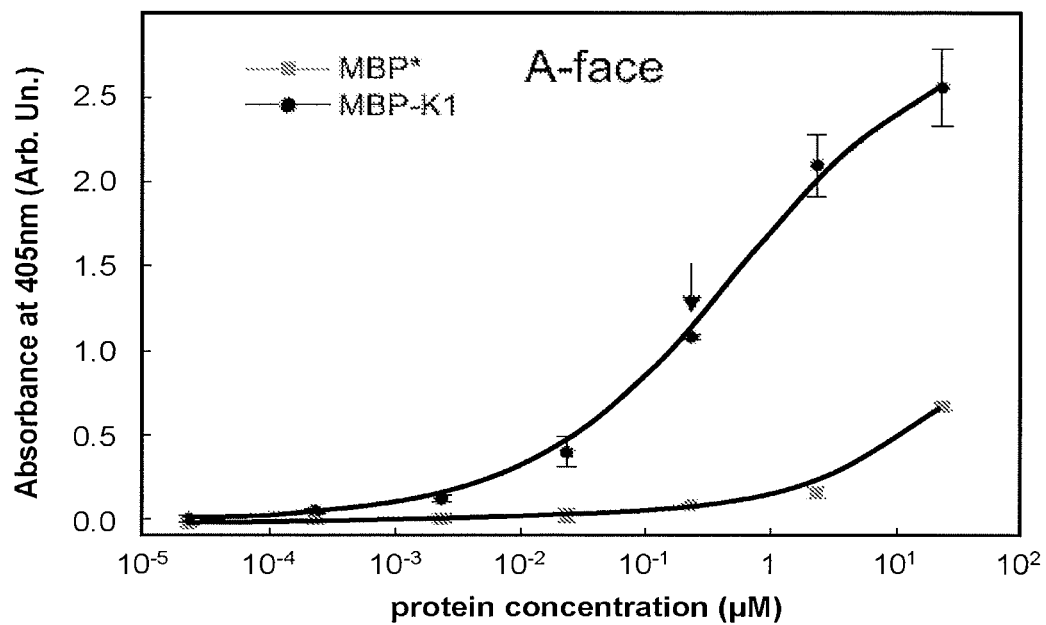
FIGS. 3A-3B show experimental results for adhesion of MBP-K1 and MBP* to the A-face of sapphire substrates performed in PBST buffer. Protein MBP-K1 contains the K1 (SEQ ID NO: 1) peptide at the end of linker at the c-terminus of maltose binding protein (MBP). Protein MBP* is the same construct minus the twelve-amino acids of K1 (SEQ ID NO: 1). Adhesion is measured through a chromogenic reaction with horse radish peroxidase (HRP), which is conjugated to an anti-MBP antibody. Absorbance is measured using ultraviolet radiation at about 405 nm and subtracted from absorbance measured for no-protein controls. (3A) Adhesion of MBP-K1 and MBP* to A-face sapphire at various dilutions of the incubation concentration. The arrow represents the peptide concentrations used for the results reported in FIG. 3B. (3B) Adhesion of MBP-K1 and MBP* to the C-, A-, and R-faces of sapphire with an incubation concentration of about 10 μg/mL (0.23 μM). Each data point represents the average and standard deviation of binding from at least two independent experiments.

In order to demonstrate applicability of the inventive peptides as affinity tags in protein bioassays, the inventors prepared two forms of a maltose binding protein (MBP), one with and one without a c-terminus K1 (SEQ ID NO: 1) peptide, and investigated each form###s binding to sapphire. Engineering and purification of MBP, a good model protein because its stability in *E. coli* leads to large expression and high yield purifications, was accomplished using the pMAL expression kit available from New England Bio labs. Binding to sapphire was measured by the activity of horse radish peroxidase (HRP) conjugated to anti-MBP antibody. The results of FIG. 3A show significantly improved binding (over several orders of magnitude) of the K1 (SEQ ID NO: 1) peptide integrated with MBP (MBP-K1) over the naive MBP (MBP*) to the A-face of sapphire. The binding of MBP-K1 was significantly more than background binding at about nanomolar concentrations and bound in similar quantities to MBP* but at about 500-1000 fold lower concentrations. Half-maximal binding for MBP-K1 occurred between about $10^{-7}$ and about $10^{-6}$M. Deriving a dissociation constant from this assay, however, is difficult for a couple reasons. First, endpoint measurements of absorbance are prone to saturation non-linearities and therefore limit the dynamic range of the signal. Second, assays were carried out in plastic wells which can exhibit intrinsic binding to the tested proteins and thereby skew quantitative results. A modified ELISA can address these issues and results from modified ELISA experiments are presented in Example 2.

Figure 3B:
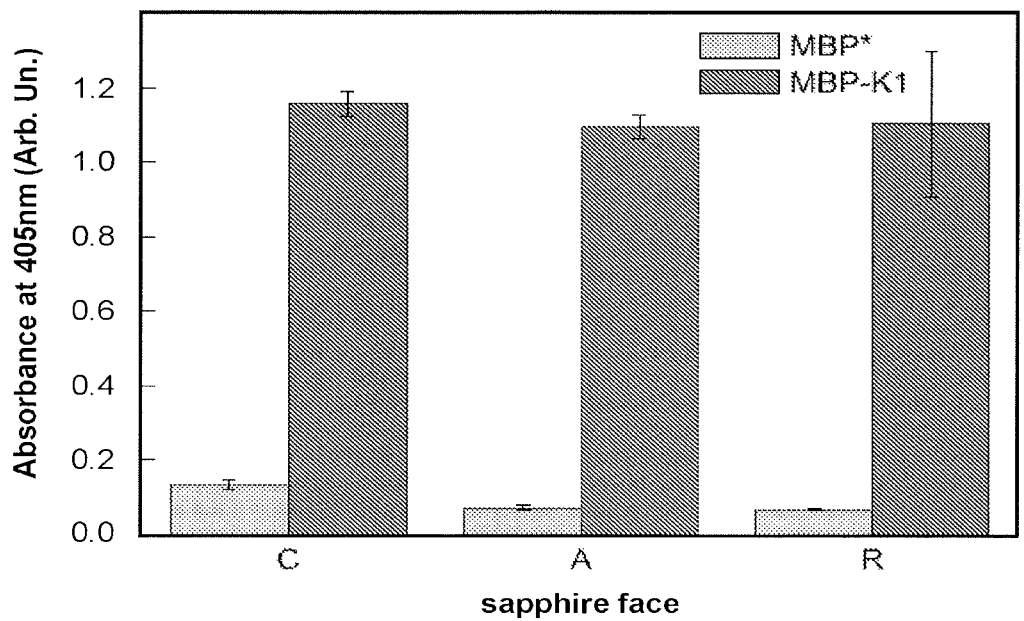

The results of FIG. 3B show the selectivity of each sapphire crystal face for MBP-K1 over MBP* at an incubation concentration of about 10 µg/mL (0.23 µM). All three faces demonstrate similar affinities for the protein, again suggesting the lack of geometric specificity of the peptides towards each surface. Interestingly, although the C-face binds MBP* better than the other faces, it also shows an improvement in binding the MBP-K1 protein. Such specificity could not be demonstrated with yeast as endogenous yeast binding to the C-face masked any potential peptide-specific binding.

For the experiments, the inventive peptides were cloned onto the c-terminus of MBP in the following manner. The pMAL-c2× vector (available from New England Biolabs, Beverly, Mass.), which encodes for the cytoplasmic expression of MBP, was digested with EcoRI and HindIII to allow for insertion of oligonucleotides on the c-terminus. Complementary oligos with EcoRI and HindIII compatible ends were annealed and ligated into the digested pMAL-c2× vector. Ligation reactions were transformed into chemically competent TOP10 *E. coli* (available from Invitrogen, Carlsbad, Calif.) and cloning success was verified through sequencing. Next, DNA from successful clones was transformed into chemically competent TB1 *E. coli* for protein expression.

The procedures for protein expression and purification were taken from the pMAL Protein Fusion and Purification Kit (available from New England Biolabs, Beverly, Mass.). Briefly, TB1 *E. coli* harboring the modified pMAL vectors were grown to mid-log phase in Glucose-Rich Media plus ampicillin before induction with IPTG to a final concentration of about 0.3 mM. After two hours of induction, cells were harvested by centrifugation and frozen overnight at about −20 degrees. The cells were then thawed in cold water and lysed by probe sonication. The crude extract was separated from the insoluble cell mater by centrifugation and applied to an amylose resin column. The bound MBP constructs were then eluted from the column with about 20 mM maltose in 1× column buffer (20 mM Tris HCl, 1 mM EDTA, 200 mM NaCl) and concentrated in 10000 MWCO Centricon Plus-20 centrifugal filtration devices (available from Millipore, Billerica, Mass.). Purification steps were monitored by SDS-PAGE and the final concentration of protein was calculated by absorbance at 280 nm and referenced with a known MBP standard from New England Bio labs.

Purification of peptide 2K1 (SEQ ID NO: 2) was carried out as described above with noted exceptions. First, pelleted cells were resuspended and lysed in 1× column buffer supplemented with approximately 1M NaCl (CB-high salt). Branched, 2000 kDa polyethyleneimine (PEI) was then added to the crude extract at a final volume ratio of about 0.1%, in order to elute and precipitate protein-bound nucleic acid. The crude extract was then washed over an amylose column with CB-high salt before eluting as mentioned above.

Certain substrates for the binding experiments were provided as follows. Synthetic sapphire ($\alpha$-$Al_2O_3$) a windows were purchased from Crystal Systems (Salem, Mass.). The three orientations obtained were the C-plate (0 0 0 1), A-plate (1 1 –2 0), and R-plate (1 –1 0 2). The sapphire was produced by a heat exchanger method, cut with a tolerance of 2°, polished to an 80/50 scratch/dig surface finish and a flatness of 10 waves per inch, as specified by the manufacturer. The sapphire substrates were refurbished for multiple experiments by exposure to fresh piranha solution (3:1 $H_2SO_4$: 30 wt % $H_2O_2$), followed by brief sonication in distilled water, and 70% (v/v) ethanol in water.

For this example, preparation and measurement of MBP bound to sapphire substrates was carried out as follows. Purified protein stocks were serially diluted to the appropriate concentration in 1×PBS containing 0.1% Tween20 (PBST). Approximately 250 µL amounts of protein solution were added to clean sapphire substrates in 48-well plates and incubated for three hours under constant agitation on an orbital shaker. Substrates were washed twice, each time transferring to new wells containing about 400 µL PBST and agitating for about 15 minutes. Substrates were then transferred to wells containing about a 2000-fold dilution of stock HRP conjugated anti-MBP monoclonal antibody (available from New England Biolabs, Beverly, Mass.) in PBS containing about 5 mg/mL bovine serum albumin (PBS-BSA) and agitated for about 30 minutes. The substrates were washed two times as before with PBS-BSA then transferred to a 96-well plate. Next, about 200 µL of chromogen solution (0.5 mg/mL ABTS (2,2'-Azino-di-(3-ethylbenz-thi-azoline sulfonic acid), 0.03% hydrogen peroxide in 0.1 M citrate buffer, pH 4.2) was added to the sapphire substrates under agitation. After about 15 minutes, the substrates were removed and the absorbance of each well was measured using ultraviolet radiation at about 405 nm wavelength (A405) on a 96-well UV/Vis plate reader (available from SpectraMAX 250, Molecular Devices, CA). Raw absorbance values were then subtracted from a background reading taken from substrates exposed to no MBP (approximately 0.2 arbitrary units (A.U.).

Example 2

Determination of Equilibrium Dissociation Constants

In order to obtain more quantitative binding affinity information, a modified ELISA was developed to assess the MBP binding to sapphire. First, sapphire substrates were incubated with tagged protein in 96-well untreated polystyrene plates. Control experiments showed minimal background binding of proteins assayed to untreated polystyrene (unlike plasma-treated polystyrene, which is discussed below). Second, the amount of anti-MBP-conjugated HRP adsorbed onto the surface was measured by an enzymatic turnover rate rather than endpoint analysis, which greatly expanded the dynamic range of the assay. With these changes, modified MBP concentrations ($[P]_0$) were titrated over several orders of magnitude, and along with enzymatic rate ($[R]$), were used to find equilibrium dissociation constants ($K_D$) by fitting a simple two parameter hyperbolic equation $$[R] = \frac{[R]_{max}[P]_0}{K_D + [P]_0} \quad (EQ. 1)$$

where $[R]_{max}$ is the other free parameter representing the enzymatic rate at saturating levels of binding. EQ. 1 represents a Langmuir model that assumes first-order, reversible kinetics in which available protein is not significantly depleted upon binding. This analysis was used to determine the $K_D$ of K1 (SEQ ID NO: 1) to sapphire and tissue culture treated polystyrene (TCT-ps). TCT-ps, created by exposing polystyrene to oxygen plasma or UV/ozone. The plasma treatment can activate the surface and leave a net negatively charged, ionized surface. Plasma treatment is used as a surface treatment in tissue culture applications due to its ability to promote cell adhesion. In this study, plasma treatment was used to provide a control amorphous surface for comparison with the structured crystalline sapphire.

Figure 4A:
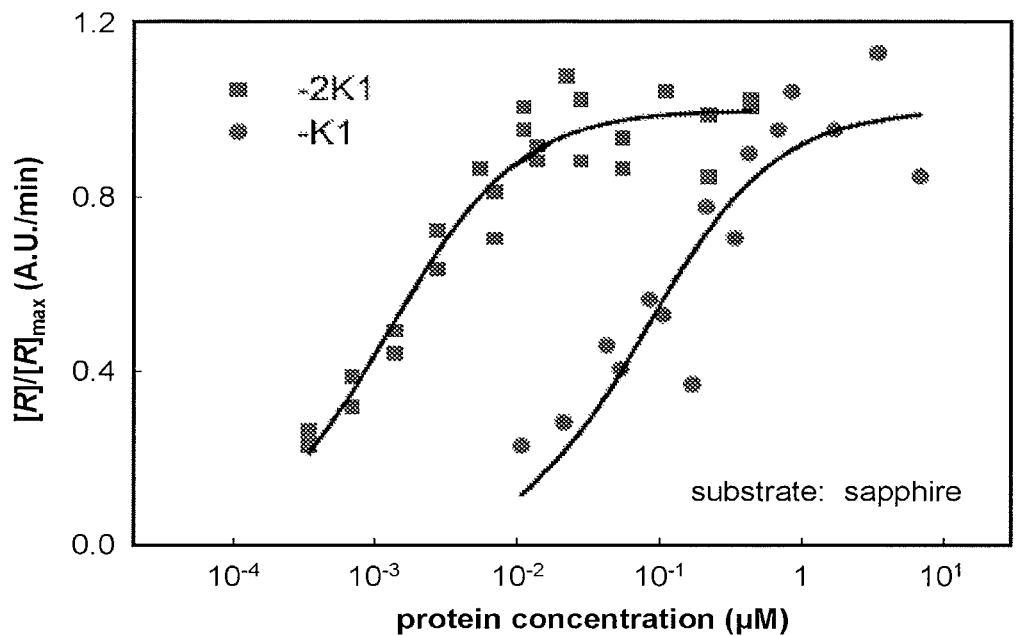
FIGS. 4A-4B show results from a modified ELISA in which peptides K1 (SEQ ID NO: 1) and 2K1 (SEQ ID NO: 2) were bound against sapphire and tissue-culture-treated polystyrene (TCT-ps). Peptides K1 (SEQ ID NO: 1) and 2K1 (SEQ ID NO: 2) were attached to the c-terminus of MBP. MBP-K1 (●) and MBP-2K1 (■) are tested against (4A) sapphire and (4B) TCT-ps.
Figure 4B:
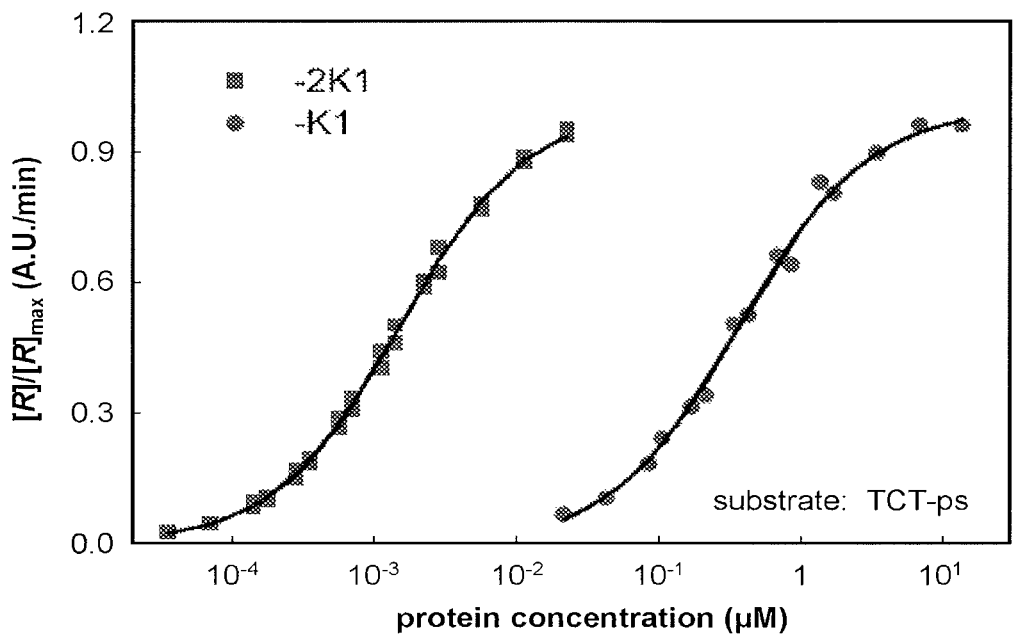

Equilibrium binding curves are shown in FIGS. 4A-4B and relevant parameters listed in Table 2. Enzymatic rates ($[R]$) are normalized to free parameter ($[R]_{max}$) of EQ. 1 and best fits represented by the solid lines. The equilibrium dissociation constant ($K_D$) obtained by fitting rate values to the two-parameter hyperbolic equation (EQ. 1) using the NLS fitting tool in OriginPro (available from OriginLab, Northhampton, Mass.). 95% confidence intervals are quoted for each parameter based on the standard error times the critical value from the t-distribution at the given confidence value. The results show that MBP-K1 attached to sapphire with a $K_D$ of about 80 nM, which is in fairly close agreement to values estimated from prior binding studies reported in FIG. 3A. MBP-K1 bound TCT-ps at $K_D$ of about 360 nM, an approximately five fold lower affinity than sapphire.

The effect of increasing positively charged amino acids on binding affinity was tested by linking two K1 (SEQ ID NO: 1) sequences together using an alanine-serine spacer. This peptide (2K1) was cloned onto the c-terminus of MBP and tested for binding to sapphire and TCT-ps (FIGS. 4A-4B). Its binding affinity over a range of protein concentrations was compared with that for MBP-K1. Doubling the length of K1 (SEQ ID NO: 1), increased the affinity towards sapphire 50 to 100-fold, with an apparent $K_D$ of about 1.3 nM. Similarly, binding to TCT-ps was dramatically increased with apparent $K_D$ of about 1.47 nM for MBP-2K1. These results demonstrate that it can be possible to modulate the affinity of these peptides by altering the number of basic amino acids. Increasing the multiplicity of peptides to increase affinity has been demonstrated by Tamerler et al., who report that tripling a selected gold-binding peptide into a 42 amino acid peptide increases equilibrium dissociation constants to $10^{-7}$-$10^{-6}$ M, with binding energies on the order of self-assembled monolayers. (See C. Tamerler, E. E. Oren, M. Duman, E. Venkatasubramanian, and M. Sarikaya, "Adsorption kinetics of an engineered gold binding peptide by surface plasmon resonance spectroscopy and a quartz crystal microbalance," *Langmuir*, Vol. 22, No. 18 (2006) pp. 7712-7718.) The nanomolar affinities demonstrated by K1 (SEQ ID NO: 1) and 2K1 (SEQ ID NO: 2) are surprisingly even greater than the 42 amino acid gold-binding peptide reported by Tamerler et al., and are on par with many antibodies.

TABLE 2

Best fit parameters to EQ. 1 from modified ELISA.

| peptide name | substrate | $K_D$ (nM) | $[R]_{max}$ (A.U./min) |
|---|---|---|---|
| K1 | sapphire[a] | 80 ± 45 | 0.34 ± .05 |
|  | TCT-ps[b] | 360 ± 4 | 1.14 ± .04 |
| 2K1 | sapphire | 1.3 ± 0.3 | 0.34 ± .01 |
|  | TCT-ps | 1.47 ± 0.07 | 1.54 ± .03 |
| R1 | sapphire | 460 ± 395 | 0.22 ± .05 |
|  | TCT-ps | 130 ± 34 | 1.29 ± .06 |
| K6 | sapphire | 320 ± 127 | 0.38 ± .05 |
|  | TCT-ps | 101 ± 23 | 1.23 ± .05 |
| H6 | Ni-NTA[c] | 30 ± 3 | 1.48 ± .06 |

[a]The A- and R-face of sapphire combined.
[b]Tissue-culture-treated polystyrene.
[c]Qiagen Ni-NTA HisSorb plates.

By creating a His-tagged MBP clone, it was possible to compare the affinity of the inventive designed sapphire binding peptides to a commonly used affinity tag for protein purification and immobilization, His-tag and nickel-NTA, under substantially similar assay conditions. Results are presented in Table 2. With a $K_D$ of approximately 30 nM, the His-tag Ni-NTA interaction was between 2K1 (SEQ ID NO: 2) and K1 (SEQ ID NO: 1). Concentrations of MBP-K1 at about $10^{-6}$ M that exhibited clear binding to sapphire were similar to concentrations used for capture of His-tagged proteins onto Ni-NTA covered plates. (D. Horakova, M. Rumlova, I. Pichova, and T. Ruml, "Luminometric method for screening retroviral protease inhibitors," *Analytical Biochemistry*, Vol. 345, No. 1 (2005) pp. 96-101.) Therefore, it should be possible to use the sapphire affinity tags for similar protein immobilization applications as His-tags. An advantage of the sapphire tags over His-tags is the lack of surface chemistry necessary to modify substrates. Certain differences between the two tags can be that the electrostatic mechanism for the inventive peptide binding may be less substrate specific and more sensitive to buffer ionic strength. Increasing the number of basic amino acids to increase affinity may lead to a trade-off between affinity and specificity, as a more basic peptide can have increased interaction with all electronegative surfaces.

In order to look more closely at the specificity of peptides towards sapphire, two more peptides were cloned onto the c-terminus of MBP: R1 (SEQ ID NO: 3) and K6. The peptide K6 comprises the sequence GGGGGGKKKKKK* (SEQ ID NO: 8) and carries a net charge of +6. Expressed on yeast, R1 (SEQ ID NO: 3) showed a significantly lower binding affinity towards A and R-faces of sapphire (FIG. 2A), while K6 did not bind under similar assay conditions (data not shown). Consistently, each peptide expressed as MBP fusions also showed a reduced affinity (approximately 4-10 fold relative to K1 (SEQ ID NO: 1)) to sapphire (Table 2). Interestingly, specificity to TCT-ps was reversed as both K6 and R1 (SEQ ID NO: 3) showed a greater affinity to TCT-ps (approximately 3-4 fold) than K1 (SEQ ID NO: 1). These results suggest that lysine preferentially interacts with the structurally organized sapphire surface anions (K1 vs. R1) and that the ability to orient all basic groups in one direction is more important for crystalline surfaces than amorphous materials (K1 vs. K6). However, further work is necessary to validate these hypotheses.

Determination of dissociation constants with modified ELISA were carried out in standard 96-well plates. Nickel-tri-nitroacetic acid binding was tested in Ni-NTA HisSorb plates (Qiagen). Tissue culture treated polystyrene binding was tested in BD-Falcon plates 35-3072. Sapphire binding was tested in untreated polystyrene plates (Corning 3651) with results averaged from both the A- and R-face. Protein stocks were serially diluted in PBST, and about 200 amounts were added to the wells followed by about a 30 minute incubation. During all incubation steps, plates were agitated at about 400 RPM on an orbital shaker. Wells were rinsed three times with PBST and exposed to about 200 µL of 1:2000 dilution of HRP conjugated anti-MBP monoclonal antibody as above. Following about a 30 minute incubation period with antibody, wells were again rinsed three times with PBST. In the case of sapphire binding, substrates were then transferred to new wells. Next, about 20 µL of 5 mg/mL ABTS was combined with about 160 µL of 0.1 M citrate buffer, pH 4.2, in each well. About 20 µL of 0.3% hydrogen peroxide was then added and absorbance measurements were immediately taken every twelve seconds for about four minutes to observe color production at 405 nm. The slope of raw absorbance versus time was used to obtain rates of color production ($Abs_{405nm}$/min) and used as a metric for the amount anti-MBP antibody in the wells.

Example 3

Non-Equilibrium Association and Dissociation

Figure 5A:
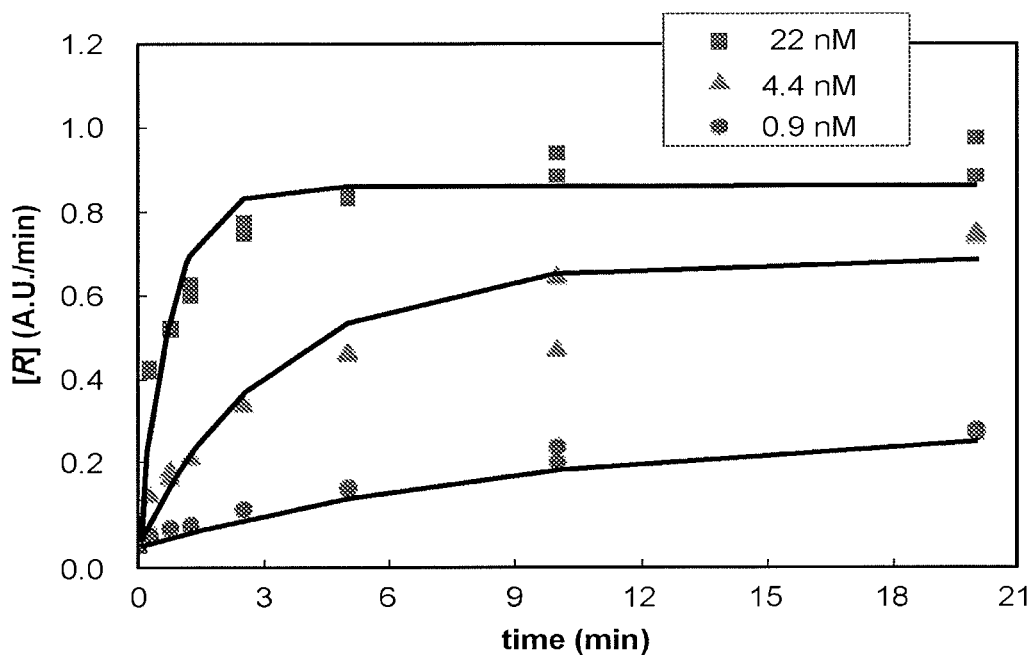
FIGS. 5A-5B indicate dynamic binding characteristics of the inventive peptide 2K1 (SEQ ID NO: 2). (5A) Association of MBP-2K1 to TCT-ps at three separate concentrations (■: about 22 nM; ▲: about 4.4 nM; ●: about 0.9 nM) measured by enzymatic rates ([R]) of HRP conjugated to anti-MBP antibody. (5B) Dissociation of the same concentrations of MBP-2K1 from TCT-ps after about 20 minutes association time. Solid lines represent best fits of the data to exponential rise and decay functions for association and dissociation data, respectively.

Knowledge of the dynamics of peptide binding can provide valuable information for certain applications and further development of systems utilizing the inventive peptides. Dynamics of peptide binding can include factors such as the time for the peptides to reach a steady-state binding equilibrium and the time for bound peptides to be released from a surface. Toward this objective, association and dissociation assays were performed with MBP-2K1 binding to TCT-polystyrene. Results from these assays are reported in FIGS. 5A-5B. Three concentrations of MBP-2K1 (about 22 nM, about 4.4 nM, and about 0.9 nM) were chosen to bracket the previously calculated $K_D$ of about 1.5 nM, and then incubated with TCT-ps for various times up to about twenty minutes. FIG. 5A indicates that all three concentrations near a steady-state binding equilibrium after about twenty minute incubations. Approximate kinetic rate parameters $k_{on}$ and $k_{off}$ were determined by fitting the data to a rising exponential using non-linear least squares regression. The fitting yields time constants for steady-state association of about 0.0024 $s^{-1}$, about 0.0042 $s^{-1}$, and about 0.022 $s^{-1}$, for each respective higher concentration. Making the pseudo-first order approximation of non-depleting protein concentrations, the kinetic rate parameters $k_{on}$ and $k_{off}$ were estimated from the slope and intercept, respectively, from a linear fit of association time constant versus concentration. This resulted in a $k_{on}$ of about $9.7 \times 10^5$ $M^{-1}$ $s^{-1}$ and a $k_{off}$ of about 0.0008 $s^{-1}$. From these values, it was possible to calculate a non-equilibrium estimate of $K_D$ of about 0.8 nM, which was approximately one-half of the measured equilibrium value of about 1.5 nM.

Figure 5B:
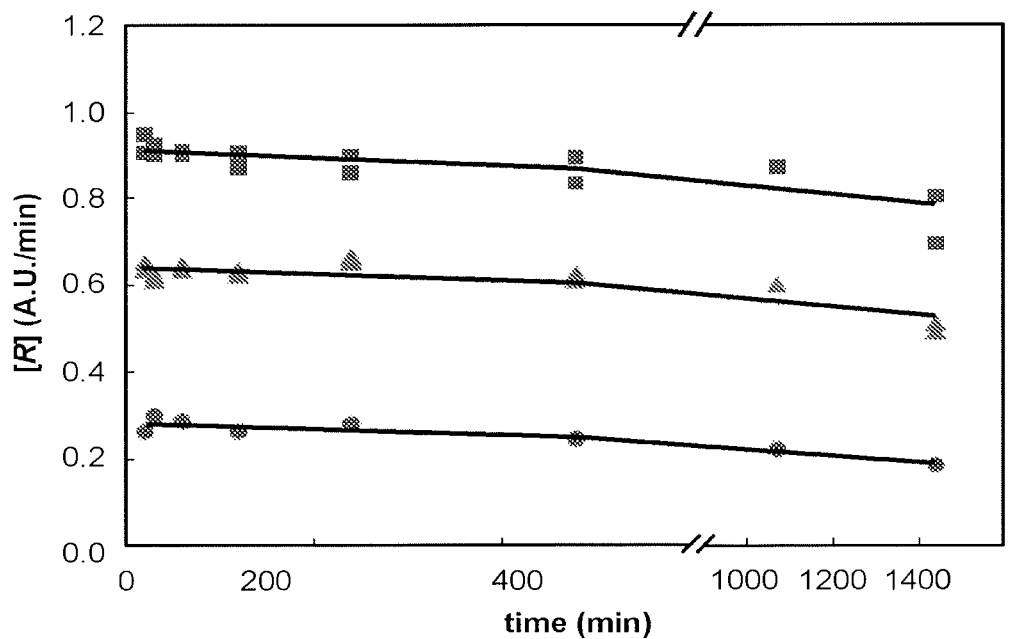

FIG. 5B indicates dissociation dynamics of MBP-2K1 from TCT-ps for the same three concentrations as used for the association study. Surprisingly, after 24 hours of washing, only about 20-30% of protein was removed from the surface. Decay time constants of about $1.8 \times 10^{-6}$ $s^{-1}$, about $2.2 \times 10^{-6}$ $s^{-1}$, and about $4.6 \times 10^{-6}$ $s^{-1}$ for each respective higher concentration, were determined by fitting the data and correspond to a decay half-life of approximately 60 hours. This data suggests that peptide 2K1 (SEQ ID NO: 2) is suitable for applications of protein surface labeling that can last up to several days. In some embodiments, the inventive peptides can provide surface labeling which persists for between about 1 hour and about 4 hours, between about 4 hours and about 8 hours, between about 8 hours and about 16 hours, between about 16 hours and about 30 hours, between about 30 hours and about 60 hours, and yet between about 60 hours and about 100 hours.

Interestingly, the decay constants from the dissociation experiment are almost three orders of magnitude slower than the estimated $k_{off}$ from the association experiment. This discrepancy might be explained by a two-step binding event in which a loosely associated state transitions to a more tightly bound state. Physically, the loosely bound state might represent the protein domains interacting with the surface and the 2K1 (SEQ ID NO: 2) peptide only partially bound, while the tightly bound state could represent a rearrangement so that the protein domains become oriented away from the surface and the 2K1 (SEQ ID NO: 2) peptide more fully complexed with the surface. The dissociation assays might only provide information about the tightly bound protein, as the loosely associated state could either by removed or transitioned to tightly bound during the numerous rinses or 20 minute antibody incubation. Therefore, the results for the dissociation experiment FIG. 5B might pertain primarily to the tightly bound state and yield a slow $k_{off}$, while the association experiment can assess the flux between the unbound, loosely bound, and tightly bound proteins, and hence yield a faster estimated $k_{off}$. Further experimentation with varying incubation times followed by dissociation timecourses might verify this two-step hypothesis and parse out individual rate parameters.

The non-equilibrium association and dissociation experiments were carried out using protein MBP-2K1 on tissue-culture-treated polystyrene (TCT-ps) 96-well plates (BD-Falcon plates 35-3072). For association experiments, protein stocks were diluted in PBST and about 150 µL amounts were added to the wells and incubated for a selected periods of time (from about 20 minutes to about 15 seconds). During all incubation steps, plates were agitated at about 400 RPM on an orbital shaker. Wells were then rinsed two times with PBST and exposed to about 150 µL of 1:2000 dilution of HRP conjugated anti-MBP monoclonal antibody as described above. Following a approximately 20-minute incubation period with antibody, wells were again rinsed two times with PBST. The amount of HRP in each well was quantified as described in Example 2. Dissociation experiments were performed in a similar manner except that about a 20-minute protein incubation period was followed by washing that varied in time over a 24-hour period. Following a 20-minute incubation period with antibody, protein that remained bound was measured through HRP enzymatic turnover. Approximate values for $k_{off}$ were determined by fitting to a decaying exponential function.

Example 4

Versatility of 2K1 (SEQ ID NO: 2) as a General Protein Affinity Tag

Figure 6A:
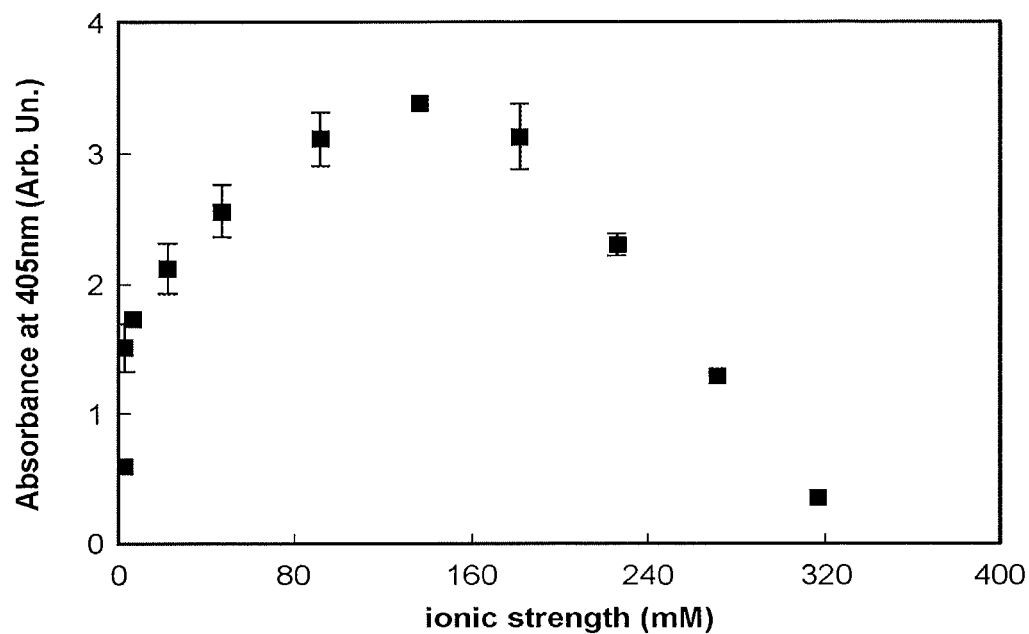
FIGS. 6A-6B demonstrate biphasic binding behavior of the inventive peptide 2K1 (SEQ ID NO: 2) and its binding to a variety of oxide surfaces. (6A) Demonstrates the effect of ionic strength on the binding of MBP-2K1 to TCT-ps. (6B) Demonstrates binding of MBP-2K1 to various oxide substrates. A: A-face sapphire; Z: Z-cut quartz (single-crystal $SiO_2$); T: thermally grown 100 nm-thick $SiO_2$ layer on Si wafer; S: standard microscope slide (borosilicate glass). Each data point represents the average and standard deviation of binding from two independent substrates. For both experiments, absorbance at 405 nm was measured after about a 10-minute incubation period in an ABTS reaction mix.

Peptide 2K1 (SEQ ID NO: 2) was characterized further to assess its utility as a general affinity tag. Results from these investigations are reported in FIGS. 6A-6B. FIG. 6A shows data representative of 2K1 (SEQ ID NO: 2) binding to TCT-ps substrates wherein the 2K1 (SEQ ID NO: 2) is suspended in various ionic strength solutions while exposed to the substrate. The protein was incubated at a final concentration of about 0.1 µg/mL in 0.1×PBST supplemented with various concentrations of NaCl. The observed binding exhibits biphasic behavior. In this case, the decrease in binding at low ionic strength can be due to repulsion of net negative charge of the MBP protein (pI about 5 with −11 net charge at neutral pH) and the negatively ionized TCT-ps surface. Maximal binding occurs near an ionic strength of about 1×PBS (166 mM), which makes the tag suitable for bioassays performed at physiological conditions. At ionic strength greater than 350 mM, binding is almost eliminated and is believed to be due to charge screening between the peptides and substrate surface. A biphasic binding property can be advantageous in that it should allow for facile refurbishing of substrates and sensors by incubation with or exposure to high salt buffers.

Figure 6B:
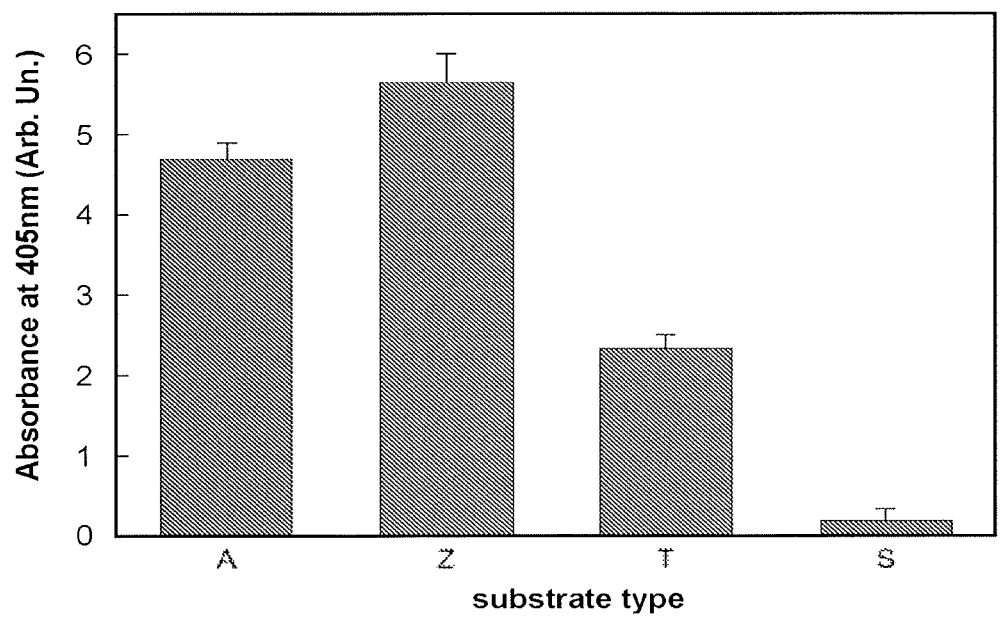

In this study, synthetic sapphire was chosen as a model metal oxide substrate material. However, many applications can require different oxide-based materials, so further experiments were carried out to assess binding of the peptide to other oxide materials. Peptide 2K1 (SEQ ID NO: 2) was tested for binding to a panel of oxide substrates, and results are shown in FIG. 6B. The inventive 2K1 (SEQ ID NO: 2) protein was incubated at a final concentration of about 1 µg/mL, in 1×PBST. Affinity of the peptide varied greatly on the various materials with a general trend of more structured substrates leading to more binding. Binding was similar between the A-face of sapphire and the C-face of single-crystalline quartz (denoted with "Z" in the FIG. 6B), both highly ordered oxide surfaces. Exposure of the peptide to a less ordered oxide, thermally grown silicon dioxide ("T") on a silicon wafer resulted in approximately half the binding level observed for quartz. Binding to amorphous silica, in the form of a borosilicate microscope slide ("S"), was observed to be almost at background levels.

It is uncertain whether binding is directly related to atomic order, or whether the atomic structure in these substrates just increased the level of surface anions (oxygen). The inventors propose the latter explanation since amorphous TCT-ps does not exhibit long-range atomic order but has been found to bind the peptides with high affinity. (See, for example, FIG. 4B.) In either case, the ability of 2K1 (SEQ ID NO: 2) to bind a variety of oxide materials increases its applicability as a general protein affinity tag.

Example 5

µPIP Patterning of MBP-2K1

Steps followed to micropattern a substrate by the method of µPIP are depicted in FIG. 7A. A PDMS mask was cleaned by sonication in 70% (v/v) ethanol in water for about 20 minutes and then allowed to dry in air. A polystyrene substrate was cleaned with three rinses of warm soapy water followed by three rinses with ethanol and ultra-pure water before drying in air. The PDMS mask was placed on polystyrene and the pair exposed to oxygen plasma for about one minute. The PDMS mask was then removed from the polystyrene substrate, and a solution of about 10 µg/mL MBP-2K1 in PBST was applied to the polystyrene surfaces for about 20 minutes. The polystyrene substrate was washed three times with about 1 mL PBST. Next, about 1 mL of anti-MBP mouse IgG, diluted 1:2000 from a 1 mg/mL stock (New England Biolabs) in PBS-BSA was incubated for about 30 minutes before washing three more times with about 1 mL PBST. A second 30 minute antibody labeling step was performed with about 1 mL of 10 µg/mL goat-anti-mouse IgG-AlexaFluor488 in PBS-BSA, followed by an additional three washes. Substrates were then imaged using fluorescein isothiocyanate (FITC) filter sets and standard fluorescent microscopy techniques.

A micrograph of a region of a substrate patterned with the affinity-tagged proteins by the method of μPIP is shown in FIG. 7A. The light-shaded areas are regions where the tagged proteins are attached to the substrate. The dark-shaded area is a region where substantially no tagged proteins are bound to the substrate.

Example 6

μCP Patterning of MBP-2K1

Steps followed to micropattern a substrate by the method of μCP are depicted in FIG. 7B. A topographically-patterned PDMS stamp was cleaned by sonication in 70% (v/v) ethanol in water for about 20 minutes and then allowed to dry in air. The PDMS stamp was then exposed to oxygen plasma for about one minute followed by about one minute exposure to ambient air. A 10 μg/mL MBP-2K1 solution in PBST was exposed to the stamp for about 15 minutes. Excess and unbound protein was washed off the stamp by submersing PDMS in ultra-pure water 3 times followed by drying under a nitrogen air stream. The stamp was then pressed onto tissue-culture-treated polystyrene substrate (TCT-ps; BD-Falcon 6-well plates, 35-3046) and left in contact for about 20 minutes. The stamp was then removed, and the substrate stained with primary and secondary antibodies as described in Example 5.

A micrograph of a region of a substrate patterned with the affinity-tagged proteins by the method of μCP is shown in FIG. 7B. The light-shaded areas are regions where the tagged proteins are attached to the substrate. The dark-shaded band is a region approximately 100 microns wide where substantially no tagged proteins are bound to the substrate. The fidelity of the line edges suggest that the patterning resolution is better than about 10 microns.

Example 7

Electronic Removal of Affinity-Tagged Proteins

Figure 8A:
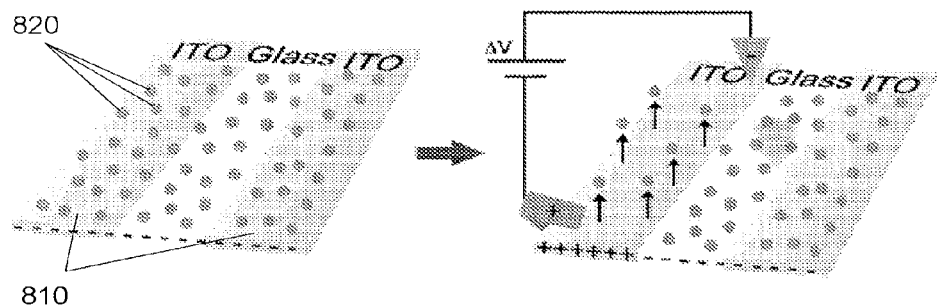
FIG. 8A depicts electrochemical modulation of affinity-tagged proteins bound to patterned indium tin oxide (ITO). Tagged proteins bound to patterned ITO electrodes (left) can be selectively desorbed by application of a positive electrical bias (right).

An experiment was carried out to investigate electrochemical desorption of affinity-tagged proteins (MBP-2K1) from indium tin oxide (ITO) substrates. Glass substrates with a thin film of ITO were obtained from Delta Technology (resistivity about 13-30 Ω-cm). To create patterned ITO electrodes on the substrates, silicon tape was used as a patterning mask. Unmasked ITO was etched away to expose the underlying glass substrate by exposure to agua regia (100 mL $H_2O$, 80 mL hydrochloric acid, 35 mL nitric acid) for about 15 minutes followed by several rinses in ultra-pure water. After removal of the silicon tape, the substrate and patterned ITO electrodes were cleaned in piranha solution (3:1 $H_2SO_4$: 30 wt % $H_2O_2$) for about 10 minutes, followed by brief sonication in ultra-pure water, and in 70% (v/v) ethanol in water. Clean ITO surfaces were connected to a voltage source with an aluminum adhesive electrode and wells were created on the clean ITO/glass substrates with 1-cm-diameter silicone gaskets (holding volume about 0.2 mL). About 180 μL of PBST was added to the well and Pt and Ag counter and reference electrodes, respectively, were lowered into the well approximately 1 mm below the top of the meniscus. Next, about 20 μL of 10 μg/mL MBP-2K1 was mixed into the well by pipette, followed by application of an electrical bias for a selected period of time. After incubation under electrical bias, the well was washed three times with PBST followed by antibody staining as described in Example 5, with all volumes adjusted to about 200 μL. Aspects of the experiment are depicted in FIG. 8A.

Figure 8B:
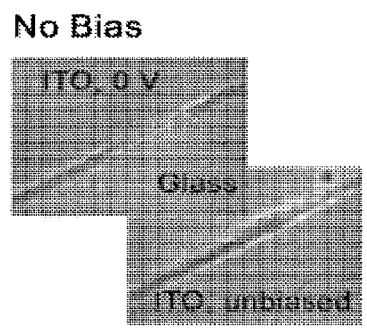
FIGS. 8B-8D are micrographs demonstrating electrochemical modulation of affinity-tagged proteins bound to patterned ITO. (8B) Immuno-stained MBP-2K1 on patterned ITO electrodes and glass with a 5 minute incubation and no applied bias. (8C) Immuno-stained MBP-2K1 with a 5 minute incubation under −0.3 V bias. (8D) Immuno-stained MBP-2K1 with a 30 second incubation under +1.8 V bias. All microscope images were obtained using a 10× objective lens.
Figure 8C:
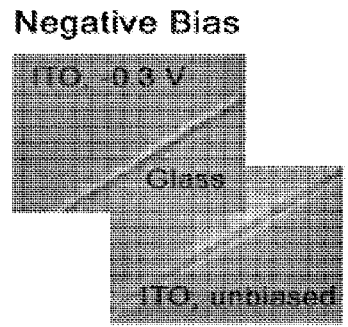
Figure 8D:
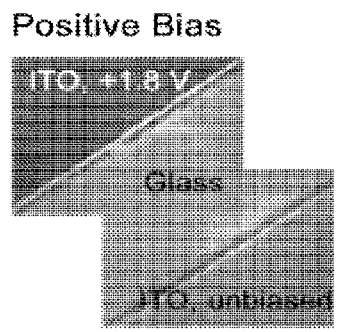

The substrate surfaces were imaged using a microscope to determine the presence of MBP-2K1. As shown in FIGS. 8B-8C, applying a 0 V and about a −0.3 V bias for about 5 minutes to the ITO during incubation did not substantially alter the binding of MBP-2K1 versus the unbiased ITO electrode. Conversely, applying about +1.8 V bias to one electrode for only about 30 seconds, FIG. 8D, significantly inhibited binding as compared to the unbiased and −0.3V biased cases. Similar conditions were used by Tang et al. to selectively remove PLL-g-PEG from ITO electrodes, although they reported significant electrolysis and degradation of the electrode at a bias of +1.8 V, which was not observed in these experiments. The discrepancy might be attributed to certain differences in electrochemical cells used. Conversely, electrolysis and destruction of the ITO electrode was seen at similar negative potentials and therefore large negative biases could not be tested.

Example 8

Functionalization of an SMR with Peptide 2K1
(SEQ ID NO: 2)

In view of results showing protein binding to thermally grown $SiO_2$ on silicon, FIG. 6B, peptide 2K1 (SEQ ID NO: 2) was selected to investigate reversible protein functionalization of a suspended mass resonator (SMR) mass sensor. An SMR was fabricated and operated as described in T. P. Burg, A. R. Mirza, N. Milovic, C. H. Tsau, G. A. Popescu, J. S. Foster, and S. R. Manalis, "Vacuum-packaged suspended microchannel resonant mass sensor for biomolecular detection," *Journal of Microelectromechanical Systems*, Vol. 15, No. 6 (2006) pp. 1466-1476, and T. P. Burg, M. Godin, S. M. Knudsen, W. Shen, G. Carlson, J. S. Foster, K. Babcock, and S. R. Manalis, "Weighing of biomolecules, single cells and single nanoparticles in fluid," *Nature*, Vol. 446, No. 7139 (2007) pp. 1066-1069. The cantilever portion of the SMR is depicted in FIG. 9A. Before application of protein to the SMR, stock solutions of MBP-2K1 and MBP* were buffer exchanged into 1×PBS with Zeba Desalt Spin columns (available from Pierce), followed by filtration through Ultra Free-MC 0.22 μm filters (available from Millipore). After cantilever surface cleaning with piranha solution, an experimental run consisted of the following steps: (1) equilibration of the sensor in 1×PBS running buffer, (2) injection of the protein using a bypass channel in the SMR, (3) measurement of cantilever resonance frequency, (4) washout of unbound protein with buffer, and (5) release of protein from oxide surfaces within the fluidic channels with a flushing rinse of high-salt buffer (0.1 M phosphate buffer, 1 M NaCl). Raw data was collected as described in Burg et al., processed, and reported. Briefly, the processing comprised adjusting the raw data by subtracting out spikes in vibrational frequency due to variations in solution density between running buffer and protein solutions, and then normalizing the data to the pre-protein resonance frequency.

Figure 9B:
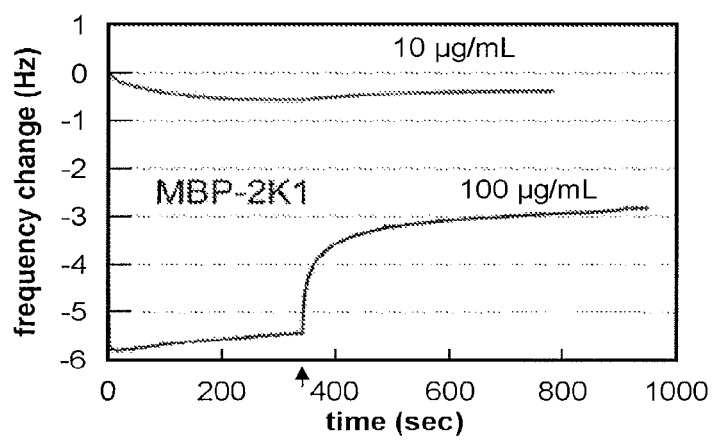
FIGS. 9B-9C show measured dose-response curves of (9B) MBP-2K1 and (9C) MBP* (MBP without the 2K1 (SEQ ID NO: 2) peptide) in 1×PBS binding to oxide surfaces in an SMR's cantilever. Protein in solution was introduced at time t=0. Flushing of the channels with high-salt buffer initiated after about 6 minutes (arrows).
Figure 9C:
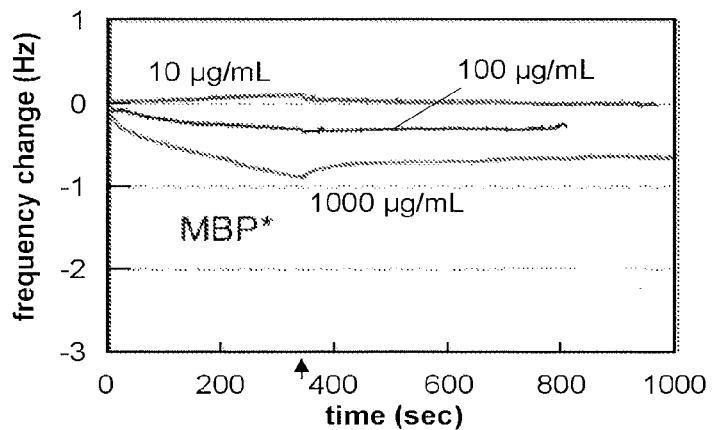

The results of FIGS. 9B-9C show specific adhesion of peptide affinity-tagged protein MBP-2K1 to the SMR cantilever. The cantilever was saturated with MBP-2K1 at an incubation concentration of about 100 μg/mL, and the bound protein resulted in about a 6 Hz frequency shift of the cantilever's resonance frequency. Conversely, MBP without 2K1 (MBP*) caused less than about a 1 Hz shift at a ten-fold higher concentration of about 1 mg/mL (FIG. 9C). This experiment and results demonstrate the potential of 2K1 (SEQ ID NO: 2) as an affinity tag for reversible functionalization in an SMR. Further experiments could optimize buffer conditions, concentrations, and incubation times to ensure consistent deposition of functionalized layers within the device.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method comprising treating an oxide or plasma-activated surface with plural peptides of the sequence GKGKGKGKGKGK (SEQ ID NO: 1) or GKGKGKGKGKGKASGKGKGKGKGKGK (SEQ ID NO: 2) wherein the peptides bind with the oxide or plasma-activated surface.

2. The method of claim 1 further comprising exposing the bound peptides to a salt buffer so that the peptides release from the oxide or plasma-activated surface.

3. The method of claim 1 wherein the peptides are integrated with biomolecules.

4. The method of claim 1 wherein the peptides are integrated with antimicrobial peptides.

5. The method of claim 1 wherein the peptides are integrated with proteins.

6. The method of claim 1 wherein the peptides are integrated with fusion proteins.

7. The method of claim 1 wherein the peptides are integrated with cells.

8. The method of claim 1 wherein the peptides are integrated with biomineralizing proteins.

9. The method of claim 1 wherein the oxide or plasma-activated surface comprises a surface of an implantable medical device.

10. The method of claim 1 wherein the oxide surface comprises a metal oxide surface of an implantable medical device.

11. The method of claim 1 wherein the oxide or plasma-activated surface comprises a surface of a cantilever of a suspended mass resonator or a surface within a chromatography or affinity-based purification apparatus.

12. The method of claim 1 wherein the oxide or plasma-activated surface comprises a surface of a component selected from a group consisting of a solar energy device, a fuel cell, a battery, a transistor, a memory component, a surface of a catalyst, a surface of a biosensor, and an electrically conductive surface.

13. The method of claim 1 wherein the oxide surface is indium tin oxide.

14. The method of claim 1 wherein the plasma-activated surface comprises polystyrene, polydimethylsiloxane, polyurethane, polycarbonate, or poly(methyl methacrylate) subjected to an oxygen plasma.

15. A fusion protein comprising the peptide having the sequence GKGKGKGKGKGK (SEQ ID NO: 1) and maltose binding protein.

16. The fusion protein of claim 15 wherein the peptide is attached to an oxide or plasma-activated surface.

17. The fusion protein of claim 15 additionally integrating an antimicrobial peptide.

18. The fusion protein of claim 15 further comprising an anti-analyte bound to the maltose binding protein.

19. The fusion protein of claim 18 wherein the peptide is attached to an oxide or plasma-activated surface.

20. The fusion protein of claim 18 wherein the anti-analyte is protein A or bFGF.

* * * * *

SEQUENCE LISTING

```
<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: A peptide which binds to an oxide surface with
      high affinity.

<400> SEQUENCE: 1

Gly Lys Gly Lys Gly Lys Gly Lys Gly Lys Gly Lys
1               5                   10

<210> SEQ ID NO 2
<211> LENGTH: 26
<212> TYPE: PRT
<213> ORGANISM: Artificial Sequence
<220> FEATURE:
<223> OTHER INFORMATION: A peptide which binds to an oxide surface with
      high affinity.

<400> SEQUENCE: 2

Gly Lys Gly Lys Gly Lys Gly Lys Gly Lys Gly Lys Ala Ser Gly Lys
1               5                   10                  15

Gly Lys Gly Lys Gly Lys Gly Lys Gly Lys
            20                  25

<210> SEQ ID NO 3
<211> LENGTH: 12
<212> TYPE: PRT
<213> ORGANISM: Artificial Sequence
<220> FEATURE:
<223> OTHER INFORMATION: Peptide variants exhibiting some binding to an
      oxide surface.
<220> FEATURE:
<221> NAME/KEY: "misc_feature"
<222> LOCATION: (2)..(2)
<223> OTHER INFORMATION: Xaa is "Lys" or "Arg"
<220> FEATURE:
<221> NAME/KEY: "misc_feature"
<222> LOCATION: (4)..(4)
<223> OTHER INFORMATION: Xaa is "Lys" or "Arg"
<220> FEATURE:
<221> NAME/KEY: "misc_feature"
<222> LOCATION: (6)..(6)
<223> OTHER INFORMATION: Xaa is "Lys" or "Arg"
<220> FEATURE:
<221> NAME/KEY: "misc_feature"
<222> LOCATION: (8)..(8)
<223> OTHER INFORMATION: Xaa is "Lys" or "Arg"
<220> FEATURE:
```

```
<221> NAME/KEY: "misc_feature"
<222> LOCATION: (10)..(10)
<223> OTHER INFORMATION: Xaa is "Lys" or "Arg"
<220> FEATURE:
<221> NAME/KEY: "misc_feature"
<222> LOCATION: (12)..(12)
<223> OTHER INFORMATION: Xaa is "Lys" or "Arg"

<400> SEQUENCE: 3

Gly Xaa Gly Xaa Gly Xaa Gly Xaa Gly Xaa Gly Xaa
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Peptide variants exhibiting some binding to an
      oxide surface.
<220> FEATURE:
<221> NAME/KEY: "misc_feature"
<222> LOCATION: (3)..(3)
<223> OTHER INFORMATION: Xaa is "Lys" or "Arg"
<220> FEATURE:
<221> NAME/KEY: "misc_feature"
<222> LOCATION: (4)..(4)
<223> OTHER INFORMATION: Xaa is "Lys" or "Arg"
<220> FEATURE:
<221> NAME/KEY: "misc_feature"
<222> LOCATION: (7)..(7)
<223> OTHER INFORMATION: Xaa is "Lys" or "Arg"
<220> FEATURE:
<221> NAME/KEY: "misc_feature"
<222> LOCATION: (8)..(8)
<223> OTHER INFORMATION: Xaa is "Lys" or "Arg"
<220> FEATURE:
<221> NAME/KEY: "misc_feature"
<222> LOCATION: (11)..(11)
<223> OTHER INFORMATION: Xaa is "Lys" or "Arg"
<220> FEATURE:
<221> NAME/KEY: "misc_feature"
<222> LOCATION: (12)..(12)
<223> OTHER INFORMATION: Xaa is "Lys" or "Arg"

<400> SEQUENCE: 4

Gly Gly Xaa Xaa Gly Gly Xaa Xaa Gly Gly Xaa Xaa
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Peptide variants exhibiting some binding to an
      oxide surface.
<220> FEATURE:
<221> NAME/KEY: "misc_feature"
<222> LOCATION: (4)..(4)
<223> OTHER INFORMATION: Xaa is "Lys" or "Arg"
<220> FEATURE:
<221> NAME/KEY: "misc_feature"
<222> LOCATION: (5)..(5)
<223> OTHER INFORMATION: Xaa is "Lys" or "Arg"
<220> FEATURE:
<221> NAME/KEY: "misc_feature"
<222> LOCATION: (6)..(6)
<223> OTHER INFORMATION: Xaa is "Lys" or "Arg"
<220> FEATURE:
<221> NAME/KEY: "misc_feature"
<222> LOCATION: (10)..(10)
<223> OTHER INFORMATION: Xaa is "Lys" or "Arg"
<220> FEATURE:
<221> NAME/KEY: "misc_feature"
<222> LOCATION: (11)..(11)
<223> OTHER INFORMATION: Xaa is "Lys" or "Arg"
```

```
<220> FEATURE:
<221> NAME/KEY: "misc_feature"
<222> LOCATION: (12)..(12)
<223> OTHER INFORMATION: Xaa is "Lys" or "Arg"

<400> SEQUENCE: 5

Gly Gly Gly Xaa Xaa Xaa Gly Gly Gly Xaa Xaa Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: A peptide exhibiting some binding to an oxide
      surface.

<400> SEQUENCE: 6

Cys Gly Lys Gly Lys Gly Lys Gly Lys Gly Lys Gly Lys Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: A peptide exhibiting some binding to an oxide
      surface.

<400> SEQUENCE: 7

Gly Lys Pro Lys Gly Lys Pro Lys Gly Lys Pro Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: A peptide exhibiting some binding to an oxide
      surface.

<400> SEQUENCE: 8

Gly Gly Gly Gly Gly Gly Lys Lys Lys Lys Lys Lys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: A flexible linking peptide with hydrophilic
      characteristics.

<400> SEQUENCE: 9

Gly Gly Gly Gly Ser Gly Gly Gly Gly Ser Gly Gly Gly Gly Ser
1               5                   10                  15
```